United States Patent
Alferness et al.

(10) Patent No.: US 6,682,476 B2
(45) Date of Patent: *Jan. 27, 2004

(54) CARDIAC DISEASE TREATMENT AND DEVICE

(75) Inventors: Clifton A. Alferness, Redmond, WA (US); Donald G. Rohrbaugh, Minnetonka, MN (US); J. Edward Shapland, Vadnais Heights, MN (US); Michael J. Girard, Lino Lakes, MN (US); Donald F. Palme, II, Princeton, MN (US); James E. Cox, Corcoran, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/279,176

(22) Filed: Oct. 23, 2002

(65) Prior Publication Data

US 2003/0045776 A1 Mar. 6, 2003

Related U.S. Application Data

(63) Continuation of application No. 09/593,251, filed on Jun. 13, 2000, now Pat. No. 6,482,146.

(51) Int. Cl.$^7$ .............................. A61F 2/00; A61F 11/00; A61F 2/24
(52) U.S. Cl. .................... 600/37; 623/904; 623/2.11
(58) Field of Search .......................... 600/37, 16, 18, 600/17; 623/3, 11, 2.11, 904; 606/151; 601/153; 604/20; 607/5; 128/898

(56) References Cited

U.S. PATENT DOCUMENTS

| 3,983,863 A | 10/1976 | Janke et al. |
| 4,048,990 A | 9/1977 | Goetz |
| 4,428,375 A | 1/1984 | Ellman |
| 4,630,597 A | 12/1986 | Kantrowitz et al. |
| 4,690,134 A | 9/1987 | Snyders |

(List continued on next page.)

FOREIGN PATENT DOCUMENTS

| DE | 295 17 393 U 1 | 3/1996 |
| EP | 0 280 564 A2 | 8/1988 |

(List continued on next page.)

OTHER PUBLICATIONS

"Supplement to Circulation", *Abstracts from the 68th Scientific Sessions*, vol. 92, No. 8, 2 pages (Oct. 15, 1995).

(List continued on next page.)

*Primary Examiner*—Eric F. Winakur
*Assistant Examiner*—Nikita R Veniaminov
(74) *Attorney, Agent, or Firm*—Merchant & Gould P.C.

(57) ABSTRACT

A jacket of biological compatible material has an internal volume dimensioned for an apex of the heart to be inserted into the volume and for the jacket to be slipped over the heart. The jacket has a longitudinal dimension between upper and lower ends sufficient for the jacket to surround a lower portion of the heart with the jacket surrounding a valvular annulus of the heart and further surrounding the lower portion to cover at least the ventricular lower extremities of the heart. The jacket is adapted to be secured to the heart with the jacket surrounding at least the valvular annulus and the ventricular lower extremities. The jacket is adjustable on the heart to snugly conform to an external geometry of the heart and assume a maximum adjusted volume for the jacket to constrain circumferential expansion of the heart beyond the maximum adjusted volume during diastole and to permit unimpeded contraction of the heart during systole.

18 Claims, 21 Drawing Sheets

U.S. PATENT DOCUMENTS

| | | | |
|---|---|---|---|
| 4,821,723 A | 4/1989 | Baker, Jr. et al. | |
| 4,878,890 A | 11/1989 | Bilweis | |
| 4,936,857 A | 6/1990 | Kulik | |
| 4,957,477 A | 9/1990 | Lundback | |
| 4,973,300 A | 11/1990 | Wright | |
| 4,976,730 A | 12/1990 | Kwan-Gett | |
| 5,057,117 A | 10/1991 | Atweh | |
| 5,087,243 A | 2/1992 | Avitall | |
| 5,131,905 A | 7/1992 | Grooters | |
| 5,150,706 A | 9/1992 | Cox et al. | |
| 5,186,711 A | 2/1993 | Epstein | |
| 5,192,314 A | 3/1993 | Daskalakis | |
| 5,256,132 A * | 10/1993 | Snyders | 600/16 |
| 5,290,217 A | 3/1994 | Campos | |
| 5,356,432 A | 10/1994 | Rutkow et al. | |
| 5,383,840 A | 1/1995 | Heilman et al. | |
| 5,385,156 A | 1/1995 | Olivia | |
| 5,429,584 A | 7/1995 | Chiu | |
| 5,507,779 A | 4/1996 | Altman | |
| 5,524,633 A | 6/1996 | Heaven et al. | |
| 5,603,337 A | 2/1997 | Jarvik | |
| 5,647,380 A | 7/1997 | Campbell et al. | |
| 5,702,343 A | 12/1997 | Alferness | |
| 5,713,954 A | 2/1998 | Rosenberg et al. | |
| 5,800,528 A | 9/1998 | Lederman et al. | |
| 5,961,440 A | 10/1999 | Schweich, Jr. et al. | |
| 5,990,378 A | 11/1999 | Ellis | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,174,279 B1 | 1/2001 | Girard | |
| 6,482,146 B1 * | 11/2002 | Alferness et al. | 600/37 |

FOREIGN PATENT DOCUMENTS

| | | |
|---|---|---|
| JP | 60-203250 A2 | 10/1985 |
| JP | 01-145066 A | 6/1989 |
| SU | 1009457 A | 4/1983 |
| WO | WO 98/29041 | 7/1998 |
| WO | WO 98/58598 | 12/1998 |
| WO | WO 99/44534 | 9/1999 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/16700 | 3/2000 |

OTHER PUBLICATIONS

Capomolla, S. et al., "Dobutamine and nitroprusside infusion in patients with severe congestive heart failure: Hemodynamic improvement by discordant effects on mitral regurgitation, left atrial function, and ventricular function", *American Heart Journal*, pp. 1089–1098 (Dec. 1997).

Capouya, E. et al., "Girdling Effect of Nonstimulated Cardiomyoplasty on Left Ventricular Function", *Ann. Thorac Surg.*, vol. 56, pp. 867–871 (1993).

Cohn, J., "The Management of Chronic Heart Failure", *The New England Journal of Medicine*, vol. 335, No. 7, pp. 490–498 (Aug. 15 1996).

Coletta, C. et al., "Prognostic value of left ventricular volume response during dobutamine stress echcardiography", *European Heart Journal*, vol. 18, pp. 1599–1605 (Oct. 1977).

Guasp, F., "Una Protesis contentiva para el tratamiento de la miocardiopatia dilatada", *Revista Espanola de Cardiologia*, vol. 51, No. 7, pp. 521–528 (Jul. 1998).

Kass, D. et al., "Reverse Remodeling From Cardiomyoplasty in Human Heart Failure External Constraint Versus Active Assist", *Circulation*, vol. 91, No. 9, pp. 2314–2318 (May 1, 1995).

Levin, H. et al., Reversal of Chronic Ventricular Dilation in Patients With End–Stage Cardiomyopathy by Prolonged Mechanical Unloading, *Circulation*, vol. 91, No. 11, pp. 2717–2720 (Jun. 1, 1995).

Oh, Jr. et al., "The Effects of Prosthetic Cardiac Binding and Adynamic Cardiomyoplasty In A Model Of Dilated Cardiomyopathy", *The Journal of Thoracic and Cardiovascular Surgery*, vol. 116, No. 1, pp. 148–153 (Jul. 1998).

Paling, D. "Warp Knitting Technology", *Columbine Press*, p. 111 (1965).

Vaynblat, M. et al., "Cardiac Binding in Experimental Heart Failure", *Ann. Thorac. Surg.*, vol. 64, 11 pages, (1997).

* cited by examiner

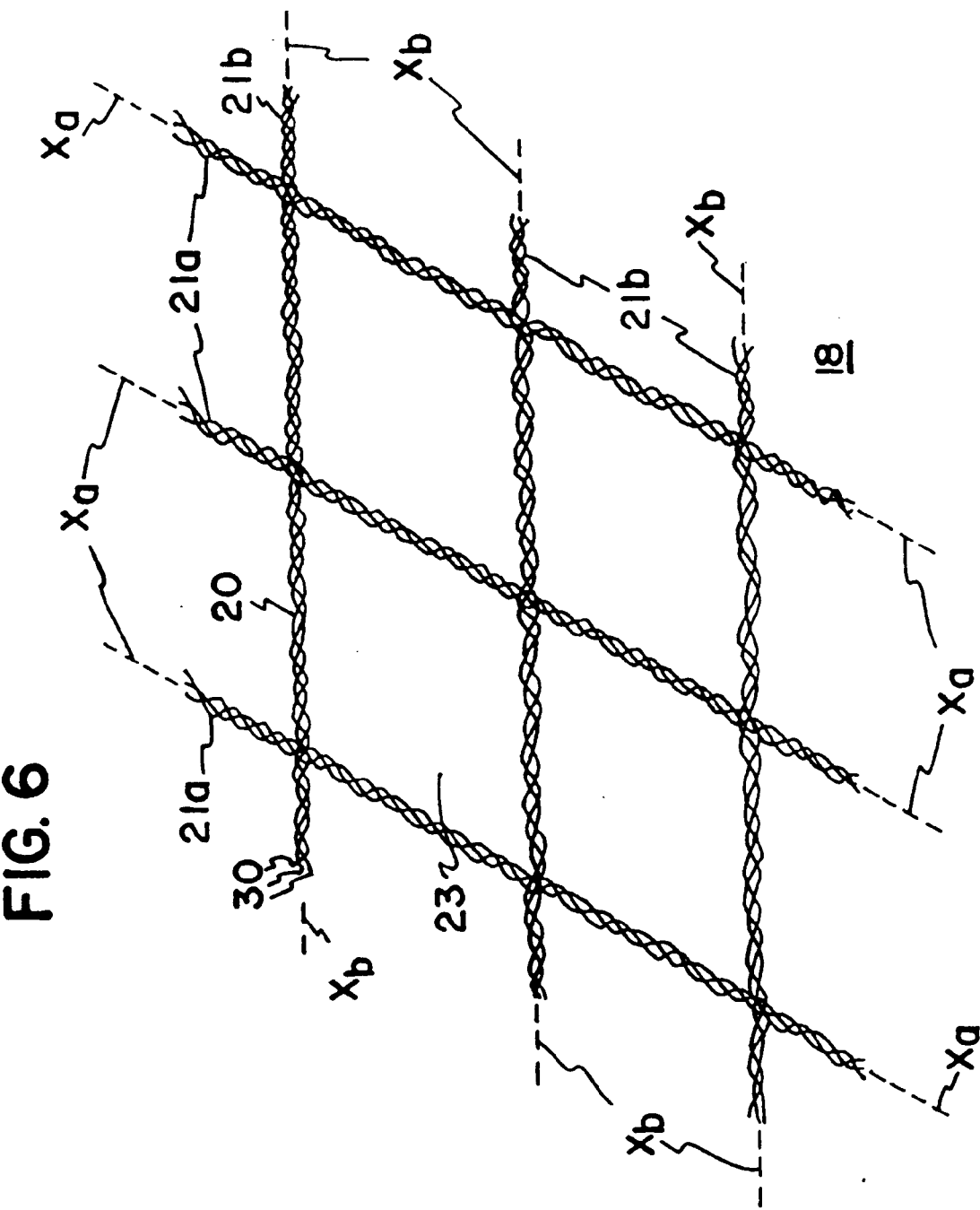

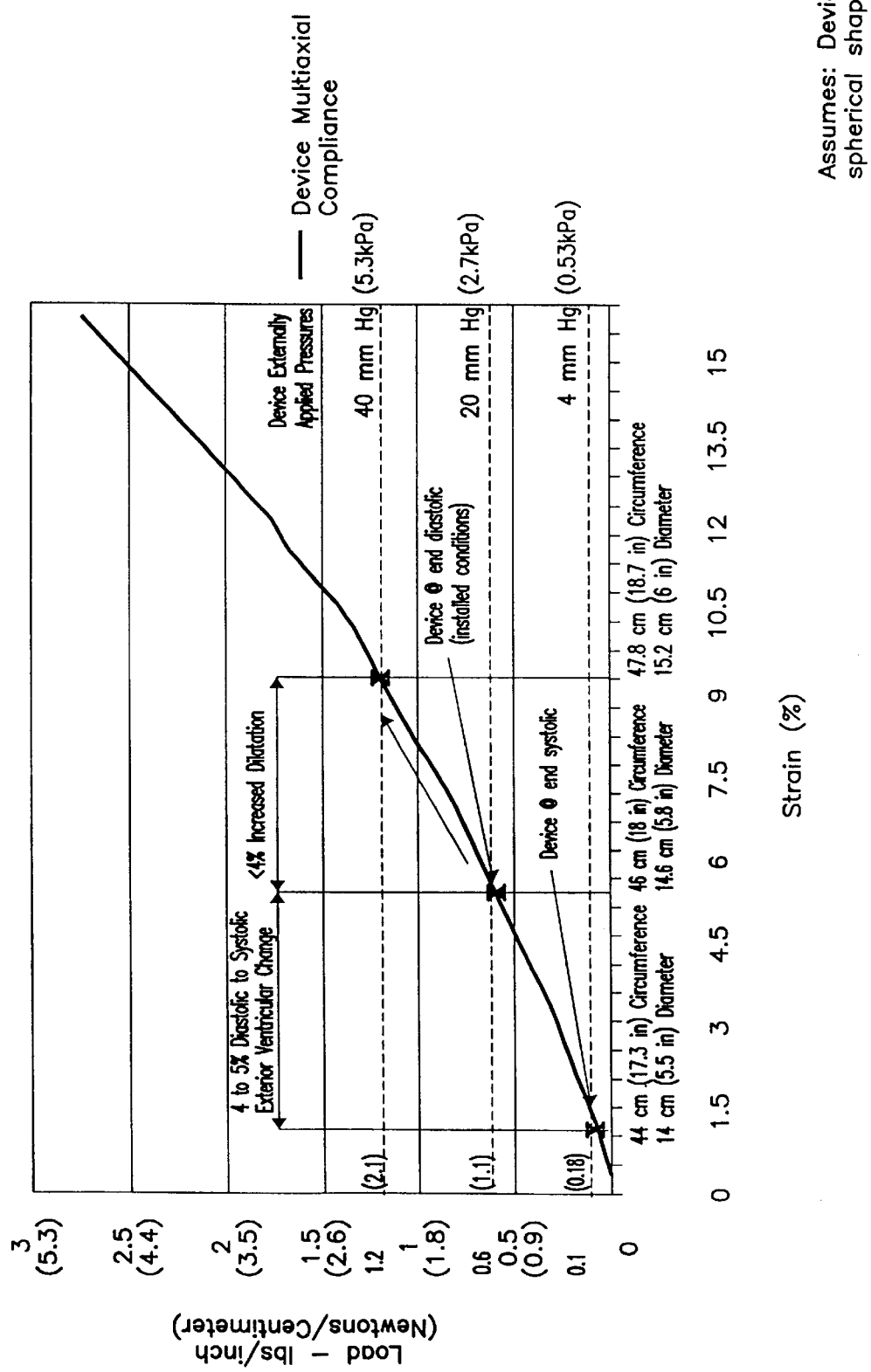

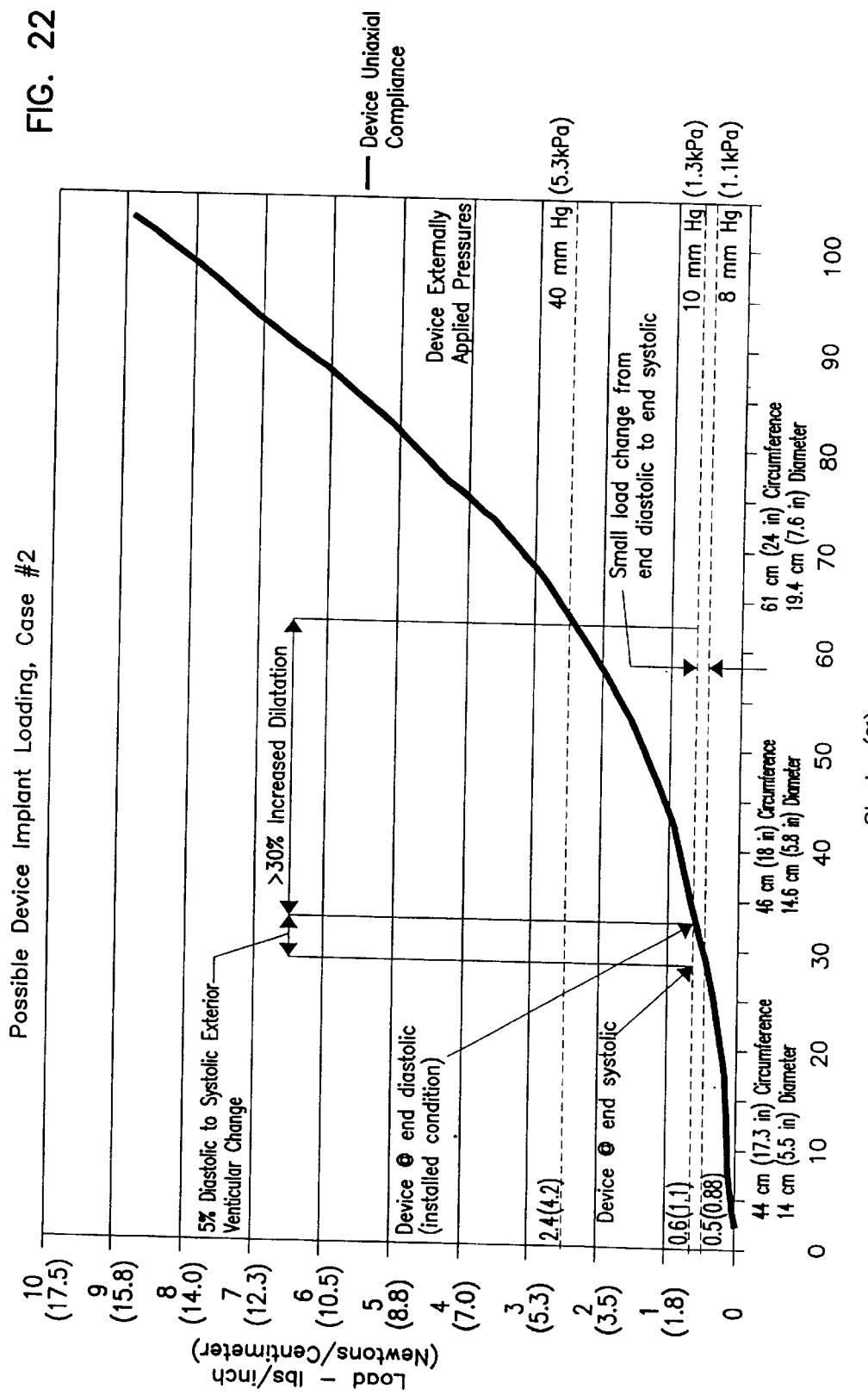

CARDIAC DISEASE TREATMENT AND DEVICE

CROSS REFERENCE TO RELATED APPLICATIONS

This application is a continuation of application Ser. No. 09/593,251 filed Jun 13, 2000. Application Ser. No. 09/593,251 now U.S. Pat. No. 6,482,146 B1 is incorporated herein by reference.

FIELD OF THE INVENTION

The present invention pertains to a device and method for treating heart disease. More particularly, the present invention is directed to a method and device for treating congestive heart disease and related valvular dysfunction.

BACKGROUND OF THE INVENTION

Congestive heart disease is a progressive and debilitating illness. The disease is characterized by a progressive enlargement of the heart.

As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Causes of congestive heart disease are not fully known. In certain instances, congestive heart disease may result from viral infections. In such cases, the heart may enlarge to such an extent that the adverse consequences of heart enlargement continue after the viral infection has passed and the disease continues its progressively debilitating course.

Patients suffering from congestive heart disease are commonly grouped into four classes (i.e., Classes I, II, III and IV). In the early stages (e.g., Classes I and II), drug therapy is the commonly proscribed treatment. Drug therapy treats the symptoms of the disease and may slow the progression of the disease. Importantly, there is no cure for congestive heart disease. Even with drug therapy, the disease will progress. Further, the drugs may have adverse side effects.

Presently, the only permanent treatment for congestive heart disease is heart transplant. To qualify, a patient must be in the later stage of the disease (e.g., Classes III and IV with Class IV patients given priority for transplant). Such patients are extremely sick individuals. Class III patients have marked physical activity limitations and Class IV patients are symptomatic even at rest.

Due to the absence of effective intermediate treatment between drug therapy and heart transplant, Class III and IV patients will have suffered terribly before qualifying for heart transplant. Further, after such suffering, the available treatment is unsatisfactory. Heart transplant procedures are very risky, extremely invasive and expensive and only shortly extend a patient's life. For example, prior to transplant, a Class IV patient may have a life expectancy of 6 months to one-year. Heart transplant may improve the expectancy to about five years.

Unfortunately, not enough hearts are available for transplant to meet the needs of congestive heart disease patients. In the United States, in excess of 35,000 transplant candidates compete for only about 2,000 transplants per year. A transplant waiting list is about 8–12 months long on average and frequently a patient may have to wait about 1–2 years for a donor heart. While the availability of donor hearts has historically increased, the rate of increase is slowing dramatically. Even if the risks and expense of heart transplant could be tolerated, this treatment option is becoming increasingly unavailable. Further, many patients do not qualify for heart transplant for failure to meet any one of a number of qualifying criteria.

Congestive heart failure has an enormous societal impact. In the United States alone, about five million people suffer from the disease (Classes I through IV combined). Alarmingly, congestive heart failure is one of the most rapidly accelerating diseases (about 400,000 new patients in the United States each year). Economic costs of the disease have been estimated at $38 billion annually.

Not surprising, substantial effort has been made to find alternative treatments for congestive heart disease. Recently, a new surgical procedure has been developed. Referred to as the Batista procedure, the surgical technique includes dissecting and removing portions of the heart in order to reduce heart volume. This is a radical, new and experimental procedure subject to substantial controversy. Furthermore, the procedure is highly invasive, risky and expensive and commonly includes other expensive procedures (such as a concurrent heart valve replacement). Also, the treatment is limited to Class IV patients and, accordingly, provides no hope to patients facing ineffective drug treatment prior to Class IV. Finally, if the procedure fails, emergency heart transplant is the only available option.

Clearly, there is a need for alternative treatments applicable to both early and later stages of the disease to either stop the progressive nature of the disease or more drastically slow the progressive nature of congestive heart disease. Unfortunately, currently developed options are experimental, costly and problematic.

Cardiomyoplasty is a recently developed treatment for earlier stage congestive heart disease (e.g., as early as Class III dilated cardiomyopathy). In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., *Reverse Remodeling From Cardiomyoplasty In Human Heart Failure: External Constraint Versus Active Assist*, 91 Circulation 2314–2318 (1995).

Even though cardiomyoplasty has demonstrated symptomatic improvement, studies suggest the procedure only minimally improves cardiac performance. The procedure is highly invasive requiring harvesting a patient's muscle and an open chest approach (i.e., sternotomy) to access the heart. Furthermore, the procedure is expensive—especially those using a paced muscle. Such procedures require costly pacemakers. The cardiomyoplasty procedure is complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole.

German Utility Model Patent Application DE 295 17 393 U1 describes a pericardium prosthesis made from a biocompatible, non-expansible material, or at least hardly expansible material which surrounds the heart. While the pericardium prosthesis prevents overexpansion of the wall of the heart, the action is deployed suddenly when the volume of the heart reaches the volume enclosed by the prosthesis. The sudden deployment may adversely affect the heart.

PCT application WO 98/58598 describes an elastic pouch for at least partially enveloping a heart. The elastic pouch always exerts the same force, substantially irrespective of its expansion, on the heart, so that the heart is always relieved of substantially the same tension irrespective of its volume. The volume of the pouch in the unexpanded state is smaller than the volume of the heart at the stage of minimum filling, thereby ensuring that the pouch is in contact with the heart in all stages of expansion. While such a force may help eject blood during systole, such a force could interfere with ventricle filling during diastole.

Commonly assigned U.S. Pat. No. 5,702,343 to Alferness dated Dec. 30, 1997 (corresponding to PCT Published Application No. WO 98/14136) teaches a jacket to constrain cardiac expansion during diastole. The present invention pertains to improvements to the invention disclosed in the '343 patent.

SUMMARY OF THE INVENTION

According to a preferred embodiment of the present invention, a method and device are disclosed for treating congestive heart disease and related cardiac complications such as valvular disorders. The invention includes a jacket of biologically compatible material. The jacket defines an internal volume dimensioned for an apex of the heart to be inserted into the volume and for the jacket to be slipped over the heart. The jacket has a longitudinal dimension between upper and lower ends sufficient for the jacket to surround a lower portion of the heart preferably between, or even including the valvular annulus of the heart and the ventricular lower extremities. The jacket is adjustable on the heart to snugly conform to an external geometry of the heart and assume a maximum adjusted volume for the jacket to constrain circumferential expansion of the heart beyond the maximum adjusted volume during diastole and to permit unimpeded contraction of the heart during systole.

The jacket is preferably constructed from a flexible material having a multi-axial expansion less than about 30% when said material is exposed to a load up to about 5 pounds per inch (9 Newtons per centimeter). More preferably, the expansion of the material along a first axis is between about 30% and 40% when exposed to a uniaxial load between about 0.1 pounds per inch (0.2 Newtons per centimeter) to about 0.5 pounds per inch (0.9 Newtons per centimeter) with no lateral constraint and the expansion of the material along a second axis perpendicular to the first axis of said material is between about 20% and 30% when exposed to a uniaxial load between about 0.1 pounds per inch (0.2 Newtons per centimeter) to about 0.5 pounds per inch (0.9 Newtons per centimeter) with no lateral constraint. Most preferably, the jacket material is oriented such a that the first axis (i.e., the more compliant direction) extends parallel to the longitudinal axis (AA–BB) of the heart.

BRIEF DESCRIPTION OF THE DRAWINGS

FIG. 6 is an enlarged view of a knit construction of the device of the present invention in a rest state;

FIG. 21 is an example of a Force-Strain plot for a spherical shaped heart with multiaxial loading of material suitable for use in the jacket of the invention; and FIG. 22 is an example of a Force-Strain plot for a cylindrical shaped heart with uniaxial loading of material suitable for use in the jacket of the invention.

DETAILED DESCRIPTION OF THE INVENTION

Congestive Heart Disease

Figure 1A:
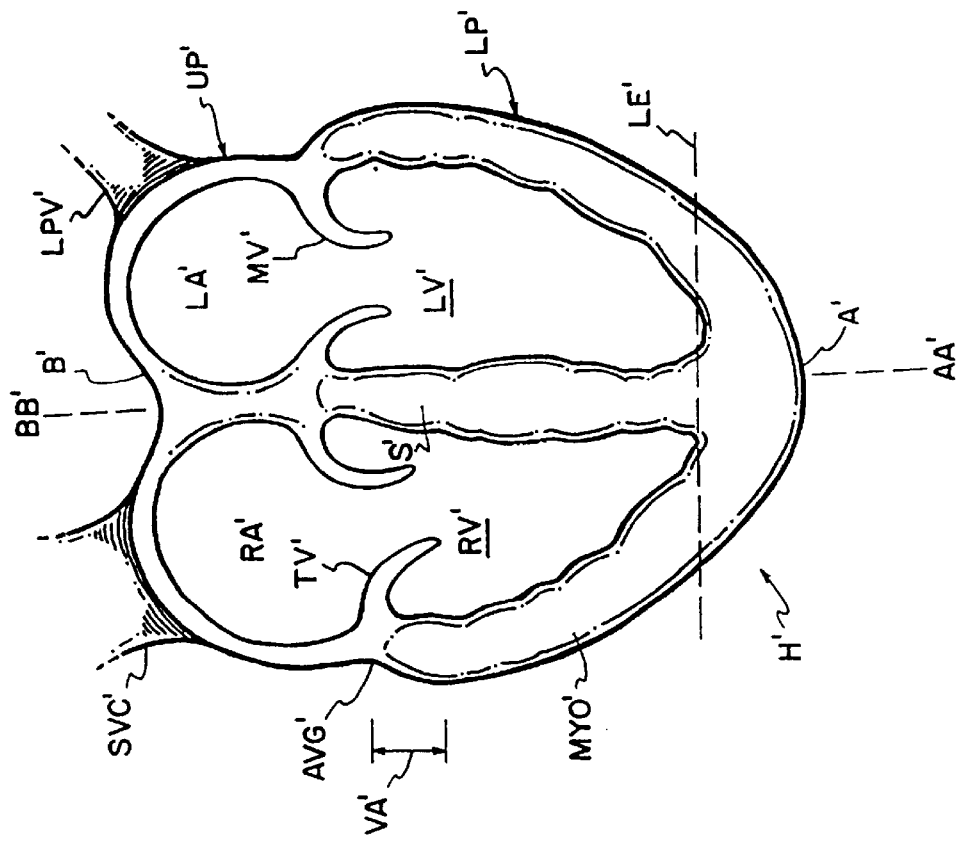
FIG. 1A is the view of FIG. 1 showing the heart during diastole.
Figure 1:
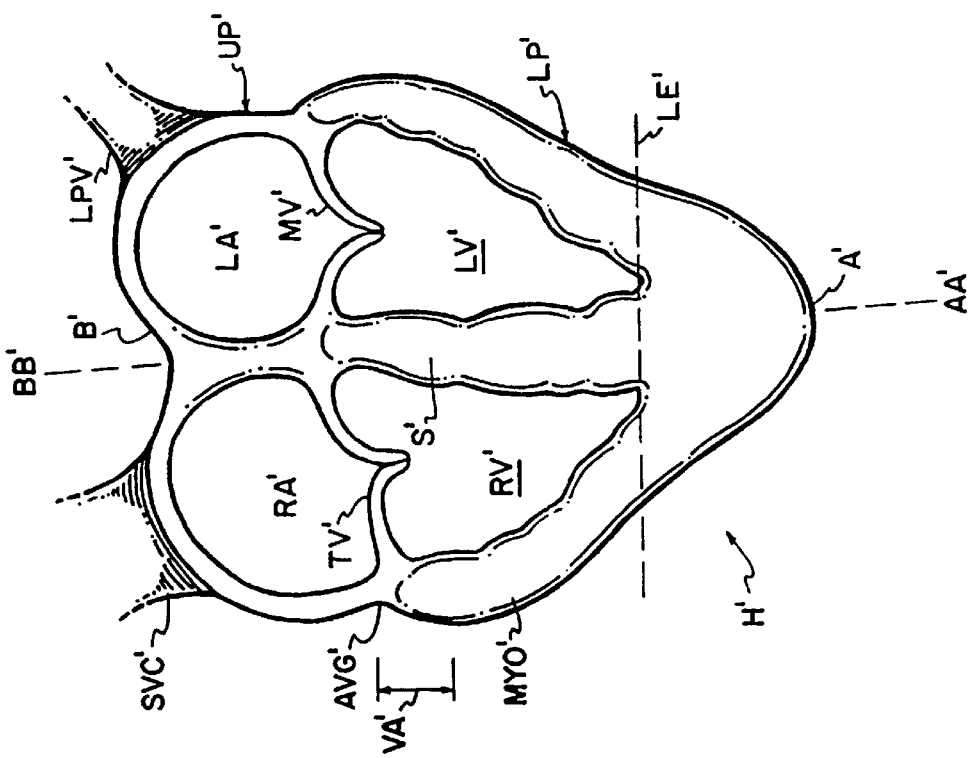
FIG. 1 is a schematic cross-sectional view of a normal, healthy human heart shown during systole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The heart H' has a length measured along a longitudinal axis AA'–BB' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V groove AVG'. Extending away from the upper portion UP' are a plurality of major blood vessels communicating with the chambers RA', RV', LA', LV'. For ease of illustration, only the superior vena cava SVC' and a left pulmonary vein LPV' are shown as being representative.

The heart H' contains valves to regulate blood flow between the chambers RA', RV', LA', LV' and between the chambers and the major vessels (e.g., the superior vena cava SVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H'.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'–BB').

The motion of the heart H' and the variation in the shape of the heart H' during contraction and expansion is complex. The amount of motion varies considerably throughout the heart H', although the external dimension of the heart H' generally reduces from about 4% to about 10% from end diastole to end systole. The motion includes a component which is parallel to the axis AA'–BB' (conveniently referred to as longitudinal expansion or contraction). The motion also includes a component perpendicular to the axis AA'–BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Figure 2B:
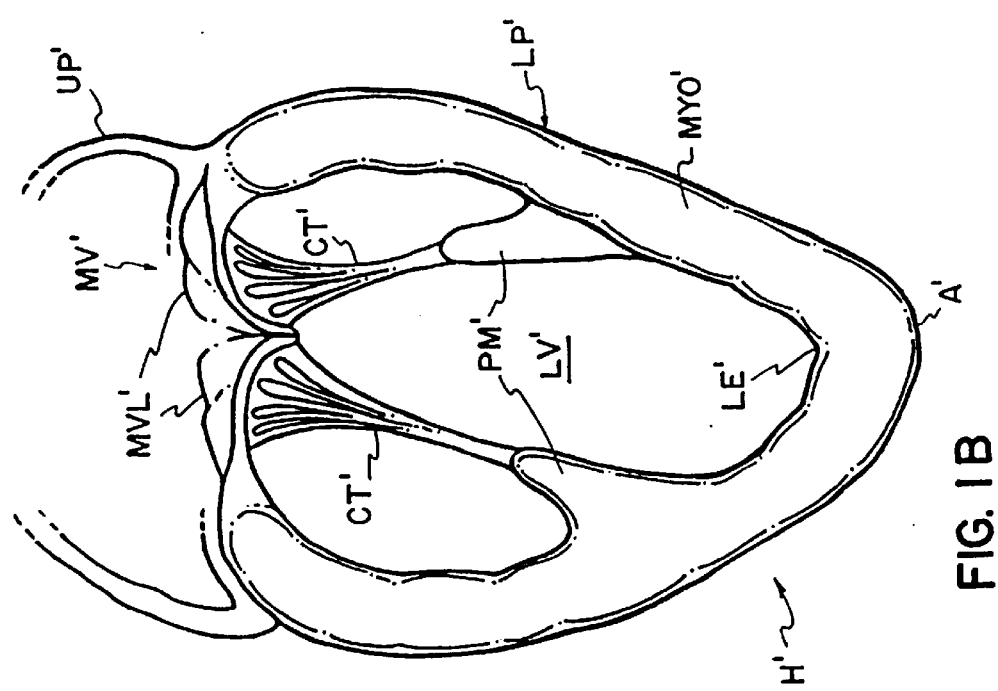
FIG. 2B is the view of FIG. 1B showing a diseased heart.
Figure 2A:
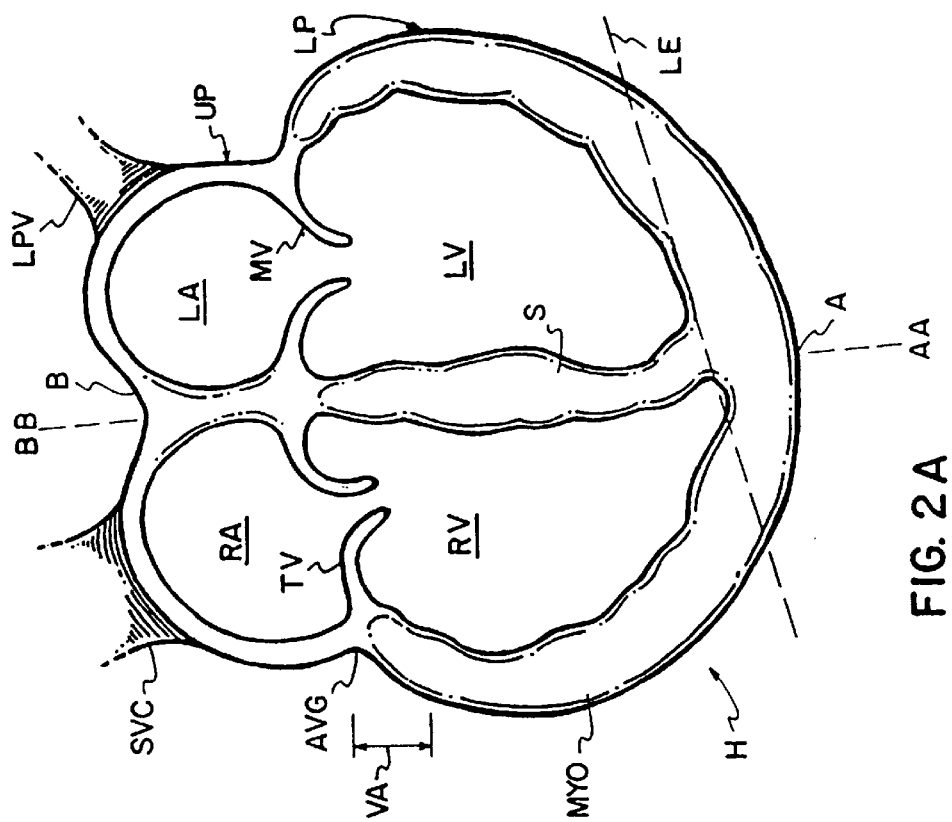
FIG. 2A is the view of FIG. 2 showing the heart during diastole.
Figure 2:
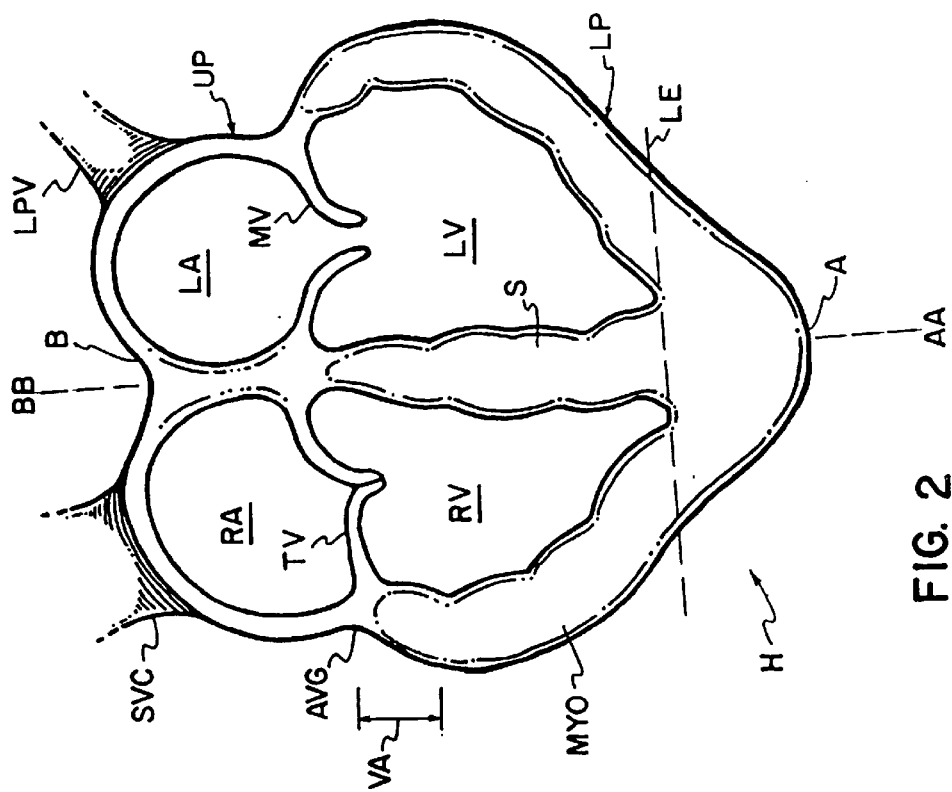
FIG. 2 is a schematic cross-sectional view of a diseased human heart shown during systole.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H bulges outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic insufficiency. In contrast to a healthy, heart H', the external dimension of the diseased heart H generally reduces from about 4% to about 6% from end diastole to end systole.

For ease of illustration, the progression of congestive heart disease has been illustrated and described with reference to a progressive enlargement of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close (as illustrated by the mitral valve MV in FIG. 2A). Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H. This is best described with reference to FIGS. 1B and 2B.

Figure 1B:
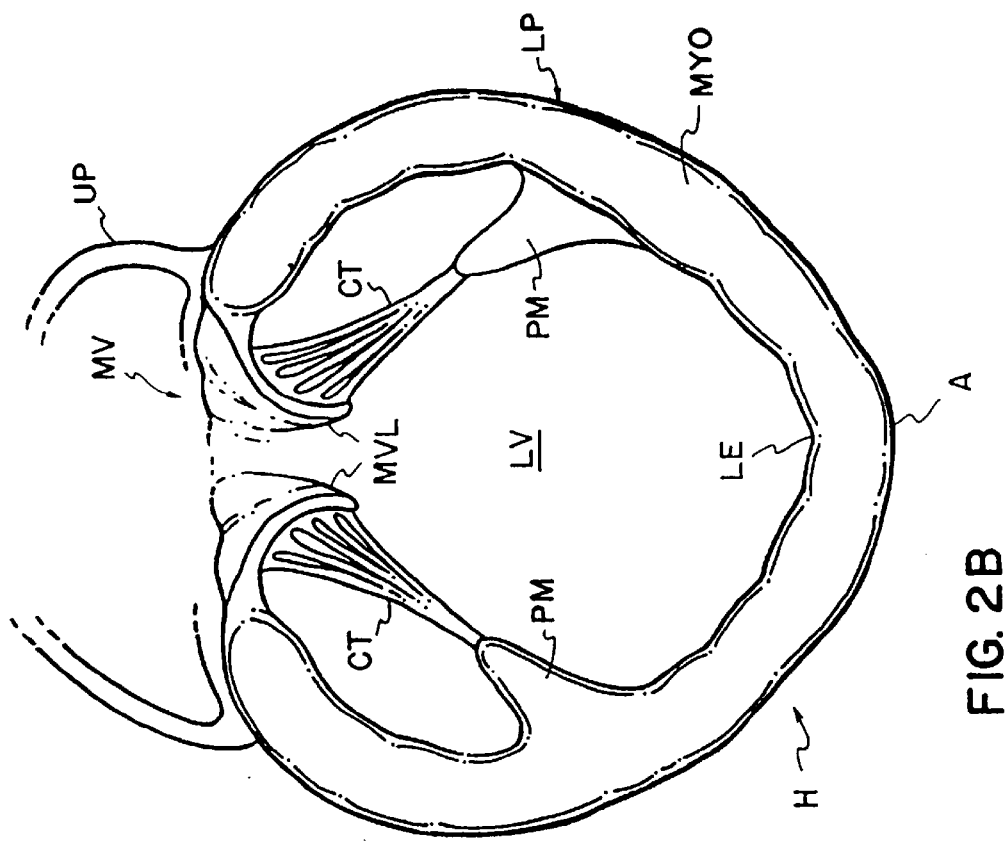
FIG. 1B is a view of a left ventricle of a healthy heart as viewed from a septum and showing a mitral valve.

FIGS. 1B and 2B show a healthy and diseased heart, respectively, left ventricle LV', LV during systole as viewed from the septum (not shown in FIGS. 1B and 2B). In a healthy heart H', the leaflets MVL' of the mitral valve MV' are urged closed by left ventricular pressure. The papillary muscles PM', PM are connected to the heart wall MYO', MYO, near the lower ventricular extremities LE', LE. The papillary muscles PM', PM pull on the leaflets MVL', MVL via connecting chordae tendineae CT', CT. Pull of the leaflets by the papillary muscles functions to prevent valve leakage in the normal heart by holding the valve leaflets in a closed position during systole. In the significantly diseased heart H, the leaflets of the mitral valve may not close sufficiently to prevent regurgitation of blood from the ventricle LV to the atrium during systole.

As shown in FIG. 1B, the geometry of the healthy heart H' is such that the myocardium MYO', papillary muscles PM' and chordae tendineae CT' cooperate to permit the mitral valve MV' to fully close. However, when the myocardium MYO bulges outwardly in the diseased heart H (FIG. 2B), the bulging results in displacement of the papillary muscles PM. This displacement acts to pull the leaflets MVL to a displaced position such that the mitral valve cannot fully close.

Having described the characteristics and problems of congestive heart disease, the treatment method and apparatus of the present invention will now be described.

Jacket

In general, the device of the invention comprises a jacket configured to surround the myocardium MYO. As used herein, "surround" means that the jacket provides reduced expansion of the heart wall during diastole by applying constraining surfaces at least at diametrically opposing aspects of the heart. In some preferred embodiments disclosed herein, the diametrically opposed surfaces are interconnected, for example, by a continuous material that can substantially encircle the external surface of the heart.

With reference now to FIGS. 3, 3A, 4 and 4A, the device of the present invention is shown as a jacket 10 of flexible, biologically compatible material. As used herein, the term "biologically compatible material" refers to material that is biologically inert such that the material does not adversely affect the surrounding tissue, for example, by eliciting excessive or injurious rejection responses, inflammation, infarction, necrosis, etc.

The jacket 10 is an enclosed material having upper and lower ends 12, 14. The jacket 10, 10' defines an internal volume 16, 16' which is completely enclosed but for the open ends 12, 12' and 14'. In the embodiment of FIG. 3, lower end 14 is closed. In the embodiment of FIG. 4, lower end 14' is open. In both embodiments, upper ends 12, 12' are open. Throughout this description, the embodiment of FIG. 3 will be discussed. Elements in common between the embodiments of FIGS. 3 and 4 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be constrained within the volume 16. The jacket 10 can be slipped around the heart H. The jacket 10 has a length L between the upper and lower ends 12, 14 sufficient for the jacket 10 to constrain the lower portion LP. The upper end 12 of the jacket 10 extends at least to the valvular annulus VA and further extends to the lower portion LP to constrain at least the lower ventricular extremities LE.

The volume 16 defined by the jacket 10 is preferably substantially the same size as or larger than the volume of the heart H, in particular the lower portion LP of the heart, at the completion of systolic contraction such that the jacket 10 exerts no or only a slight pressure on the heart at end systole. Preferably, the pressure on the heart at end systole is no more than 10 mm Hg (1.3 kPa), more preferably no more than 5 mm Hg (0.66 kPa), most preferably no more than 2 mm Hg (0.27 kPa).

Generally, the jacket 10 is adjusted to a snug fit encompassing the external volume of the heart H during diastole such that the jacket 10 constrains enlargement of the heart H during diastole without significantly assisting contraction during systole. The amount of assistance during systole can be characterized by the pressure exerted by the jacket 10 on the heart H during systole. A jacket 10 that does not significantly assist contraction during systole will not exert significant pressure on the heart H at completion of systolic contraction.

If the enlargement of the external dimension of the heart H is considered to be zero percent (0%) at completion of systole (end systole) and one hundred percent (100%) at completion of diastole (end diastole), the jacket 10 preferably exerts pressure between about 4 mm Hg (0.53 kPa) and 40 mm Hg (5.3 kPa), more typically between about 4 mm Hg (0.53 kPa) and 20 mm Hg (2.7 kPa) when the enlargement of the external dimension of the heart is between 50% and 100%. In contrast, when the enlargement of the external dimension of the heart H is below 50%, it is preferred that the jacket 10 exert a pressure between about 2 mmHg (0.27 kPa) and about 20 mmHg (2.7 kPa), preferably no more than 10 mm Hg (1.3 kPa) on the heart H. It is noted that a jacket 10 that exerts a higher pressure (e.g., closer to 40 mm Hg (5.3 kPa)) at end diastole is likely to exert a higher pressure (e.g., closer to 10 mm Hg (1.3 kPa)) at end systole than a jacket that exerts a lower pressure (e.g., closer to 5 mm Hg (0.66 kPa)) at end diastole.

Since enlargement of the lower portion LP is most troublesome, in a preferred embodiment, the jacket 10 may be sized so that the upper end 12 can reside in the A-V groove AVG. Where it is desired to constrain enlargement of the upper portion UP, the jacket 10 may be extended to cover the upper portion UP.

Sizing the jacket 10 for the upper end 12 to terminate at the A-V groove AVG is desirable for a number of reasons. First, the groove AVG is a readily identifiable anatomical feature to assist a surgeon in placing the jacket 10. By placing the upper end 12 in the A-V groove AVG, the surgeon is assured the jacket 10 will provide sufficient constraint at the valvular annulus VA. The A-V groove AVG and the major vessels act as natural stops for placement of the jacket 10 while assuring coverage of the valvular annulus VA. Using such features as natural stops is particularly beneficial in minimally invasive surgeries where a surgeon's vision may be obscured or limited.

When the parietal pericardium is opened, the lower portion LP is free of obstructions for applying the jacket 10 over the apex A. If, however, the parietal pericardium is intact, the diaphragmatic attachment (to the parietal pericardium inhibits application of the jacket over the apex A of the heart. In this situation, the jacket can be opened along a line extending from the upper end 12' to the lower end 14' of jacket 10'. The jacket can then be applied around the pericardial surface of the heart and the opposing edges of the opened line secured together after placed on the heart. Systems for securing the opposing edges are disclosed in, for example, U.S. Pat. No. 5,702,343, the entire disclosure of which is incorporated herein by reference. The lower end 14' can then be secured to the diaphragm or associated tissues using, for example, sutures, staples, etc.

Figure 3A:
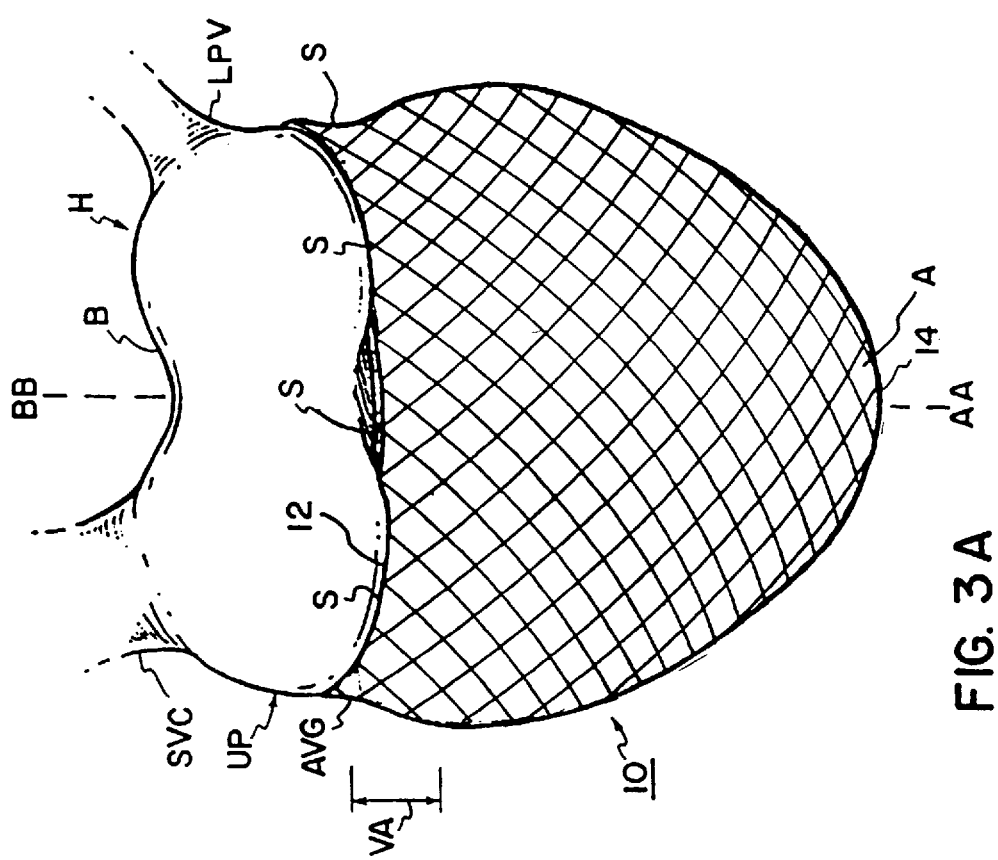
FIG. 3A is a side elevation view of a diseased heart in diastole with the device of FIG. 3 in place.
Figure 3:
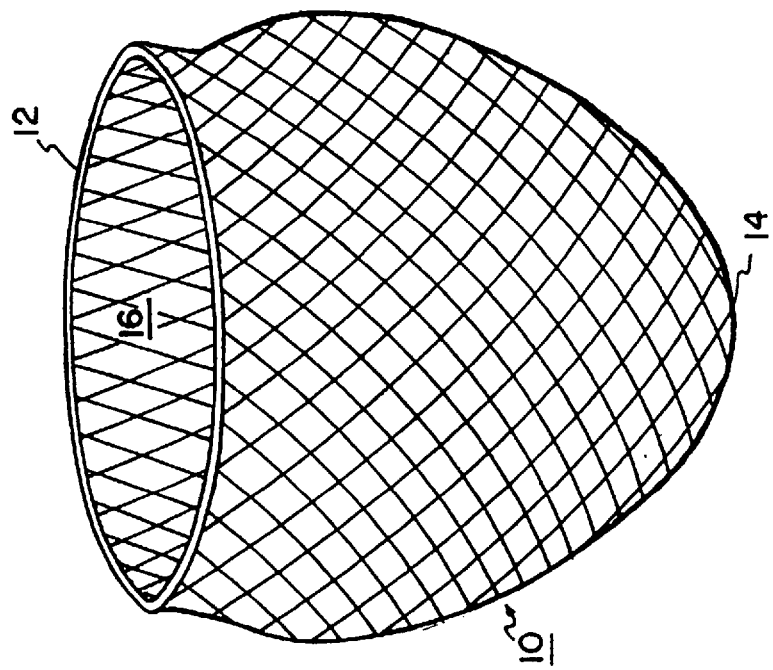
FIG. 3 is a perspective view of a first embodiment of a cardiac constraint device according to the present invention.
Figure 4A:
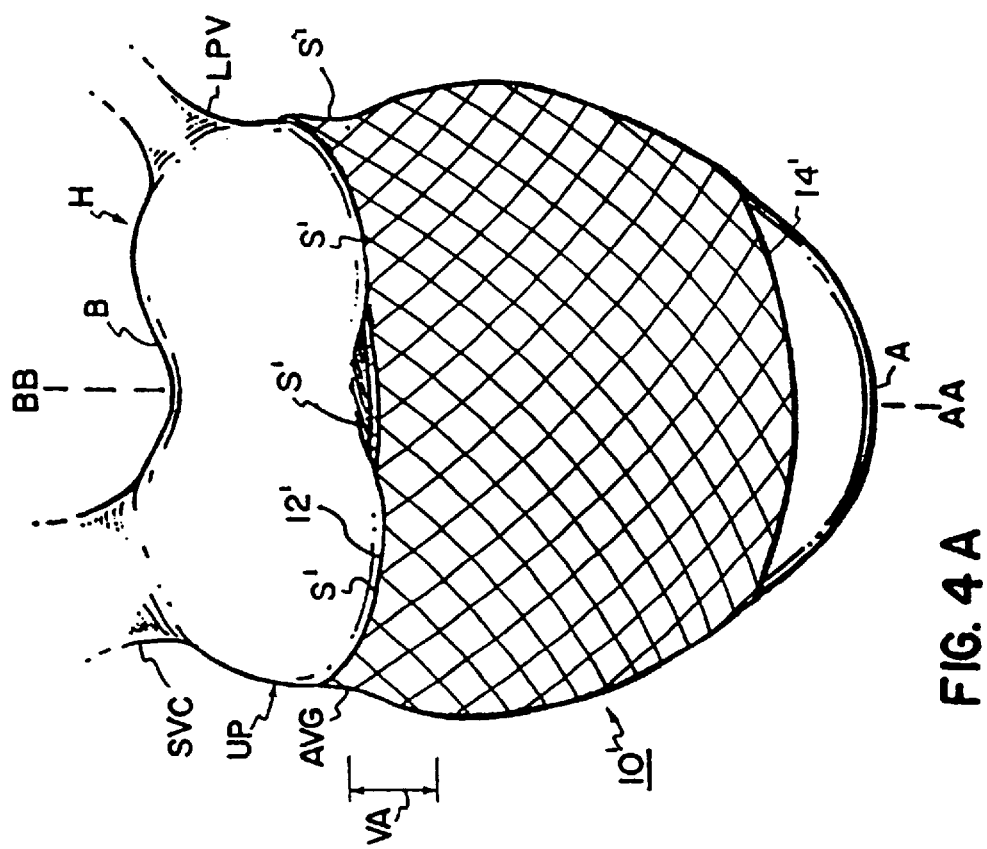
FIG. 4A is a side elevation view of a diseased heart in diastole with the device of FIG. 4 in place.
Figure 4:
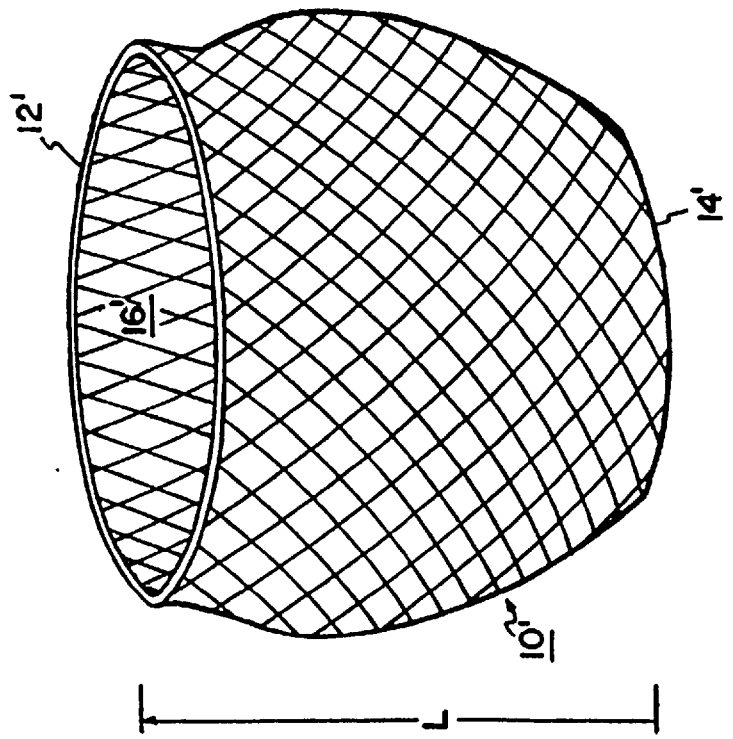
FIG. 4 is a perspective view of a second embodiment of a cardiac constraint device according to the present invention.

In the embodiment of FIGS. 3 and 3A, the lower end 14 is closed and the length L is sized for the apex A of the heart H to be received within the lower end 14 when the upper end 12 is placed at the A-V groove AVG. In the embodiment of FIGS. 4 and 4A, the lower end 14' is open and the length L' is sized for the apex A of the heart H to protrude beyond the lower end 14' when the upper end 12' is placed at the A-V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10'. Such placement is desirable for the jacket 10, 10' to present a constraint against enlargement of the ventricular walls of the heart H.

After the jacket 10 is positioned on the heart H as described above, the jacket 10 is secured to the heart. Preferably, the jacket 10 is secured to the heart H through sutures. The jacket 10 is sutured to the heart H at suture locations S circumferentially spaced along the upper end 12. While a surgeon may elect to add additional suture locations to prevent shifting of the jacket 10 after placement, the number of such locations S is preferably limited so that the jacket 10 does not restrict contraction of the heart H during systole.

Figure 5:
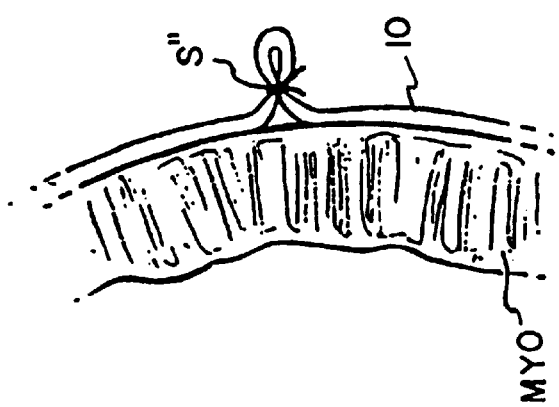
FIG. 5 is a cross-sectional view of a device of the present invention overlying a myocardium and with the material of the device gathered for a snug fit.

To permit the jacket 10 to be easily placed on the heart H, the volume and shape of the jacket 10 are larger than the lower portion LP during diastole. So sized, the jacket 10 may be easily slipped around the heart H. Once placed, the jacket's volume and shape are adjusted for the jacket 10 to snugly conform to the external geometry of the heart H during diastole. Such sizing is easily accomplished due to the construction of the jacket 10. For example, excess material of the jacket 10 can be gathered and sutured S" (FIG. 5) to reduce the volume of the jacket 10 and conform the jacket 10 to the shape of the heart H during diastole. Such shape represents a maximum adjusted volume. The jacket 10 constrains enlargement of the heart H beyond the maximum adjusted volume while preventing restricted contraction of the heart H during systole. As an alternative to gathering of FIG. 5, the jacket 10 can be provided with other ways of adjusting volume. For example, as disclosed in U.S. Pat. No. 5,702,343, the jacket can be provided with a slot. The edges of the slot can be drawn together to reduce the volume of the jacket.

The volume of the jacket can be adjusted prior to, during, or after application of the device to the heart. In one embodiment, the heart is treated with a therapeutic agent, such as a drug to decrease the size of the heart, prior to application of the jacket. In this embodiment, the therapeutic agent acts to reduce the overall size of the heart prior to surgery, and the jacket is thereafter applied to the reduced heart. Alternatively, the present invention can be used to reduce heart size at the time of placement in addition to preventing further enlargement. For example, the device can be placed on the heart and sized snugly to urge the heart to a reduced size. More preferably, the heart size can be reduced at the time of jacket placement through drugs, for example dobutamine, dopamine or epinephrine or any other positive inotropic agents, or surgical procedure to reduce the heart size. The jacket of the present invention is then snugly placed on the reduced sized heart and constrains enlargement beyond the reduced size.

The jacket 10 is adjusted to a snug fit on the heart H during diastole. Care is taken to avoid tightening the jacket 10 too much such that cardiac function is impaired. During diastole, the left ventricle LV fills with blood. If the jacket 10 is too tight, the left ventricle LV may not adequately expand and left ventricular pressure will rise. During the fitting of the jacket 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 1 mm Hg (0.13 kPa) to 3 mm Hg (0.40 kPa) can be tolerated, the jacket 10 is snugly fit on the heart H but not so tight as to cause a significant increase in left ventricular pressure during diastole.

Furthermore, because the wall of the right ventricle RV tends to be thinner than the wall of the left ventricle LV and the pressure in the right ventricle RV tends to be lower than the pressure in the left ventricle LV, the pressure exerted by the jacket 10 on the heart H is preferably not greater than the end diastolic pressure of the right ventricle RV. If the pressure exerted by the jacket 10 is greater than the pressure of the right ventricle RV, expansion and/or filling of the right ventricle RV may be compromised. Generally, a jacket 10 that imposes between about a 5% to about a 10% reduction in maximum diastolic volume serves to reduce cardiac volume without compromising cardiac function. Generally, excessive pressure exerted by the jacket 10 on the heart H results in decreased cardiac output, increased central venous pressure, and/or decreased systolic pressure.

The jacket 10 can be used in early stages of congestive heart disease. For patients facing heart enlargement due to viral infection, the jacket 10 permits constraint of the heart H for a sufficient time to permit the viral infection to pass. In addition to preventing further heart enlargement, the jacket 10 treats valvular disorders by constraining circumferential enlargement of the valvular annulus and deformation of the ventricular walls, causing displacement of the papillary muscles PM and chordae tendineae CT. Preventing displacement of these heart elements is important for allowing the leaflets MVL to fully close.

The fabric 18 of the jacket 10 is preferably tear and run resistant. In the event of a material defect or inadvertent tear, such a defect or tear is restricted from propagation by reason of the knit construction.

Material

Preferably the jacket 10 is constructed from a compliant, biocompatible material. As used herein, the term "compliant" refers to a material that can expand in response to a force. "Compliance" refers to the displacement (in inches or centimeters) or strain (inches/inch or cm/cm) per a unit load (in pounds or kilograms) or load per unit width (in pounds per inch or kilograms per centimeter) for a material. "Elasticity" refers to the ability of the deformed material to return to its initial state after the deforming load is removed.

The compliance of the device is influenced by the fabric stitch and fabrication processing as well as interaction with the tissue after implantation. The multiaxial expansion of the material is generally less than about 30%, more typically less than about 25%, most typically between about 10% and 20% as the material is exposed to a load up to about 5 pounds per inch (9 N/cm) more typically between about 1 pound per inch (1.8 N/cm) and 3 pounds per inch (5 N/cm). As used herein, the term "uniaxial expansion" refers to the expansion of a material along only one axis. The term "biaxial expansion" refers to the expansion of a material along a first axis and a second axis, typically the second axis is perpendicular to the first axis. The term "multiaxial expansion" refers expansion of a material along at least a first and a second axis and includes expansion along more than two axes.

The compliance of the material allows the jacket to be implanted without gaps and an insignificant load at end diastole. The compliance of the device along with the compliance of the heart allows the device to conform nicely to the irregular and unique shape of each heart.

Figure 8:
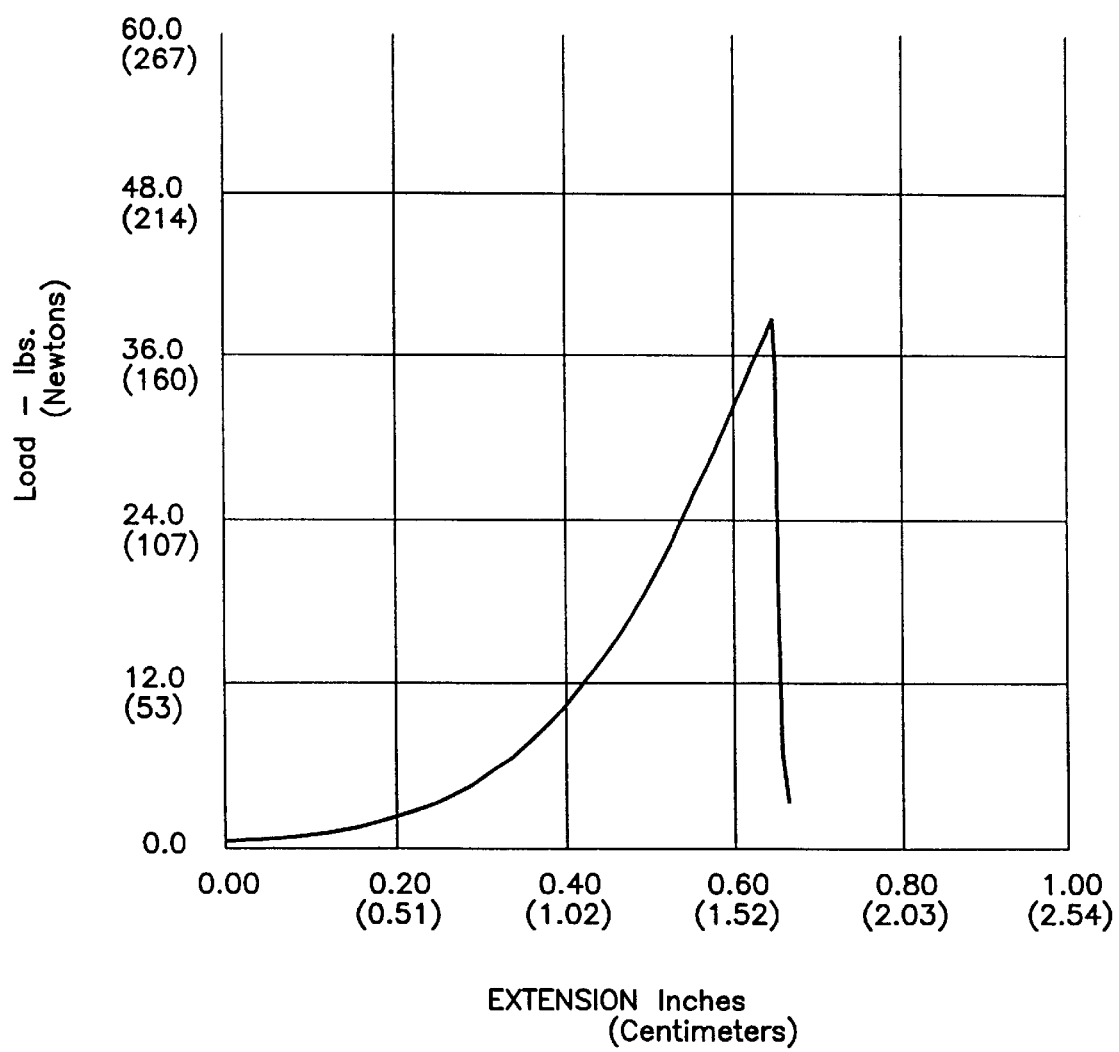
FIG. 8 shows a Force-Displacement plot of a material suitable for use in the jacket of the invention.

FIG. 8 is a graph generated from data of a ball burst test using a 1.75 inch diameter test area of sample material from the jacket of the invention. The test was performed according to ASTM D3787-89. According to this test, a ball is pressed against the center of the material with a measured force. As the load on the material is increased from 0 pounds (0 Newtons) to 36 pounds (160 Newtons), the material expands multiaxially. The initial part of the curve, up to about 5 pounds (22 Newtons) and 0.30 in (0.76 cm) deformation, has a shallow (somewhat horizontal) slope. As the load is increased above 5 pounds (22 Newtons), the slope becomes more steep (i.e, more vertical). At a load of just over 36 pounds (160 Newtons), the fabric reaches its load capacity and fails.

The force exerted by the heart during diastolic filling is small, e.g., less than 5 pounds (22 Newtons) of equivalent burst load. The normal diastolic load is more typically equivalent to a 1 to 3 pound (4 to 13 Newtons) ball burst load. Therefore, in use, the multiaxial expansion of the jacket 10 material remains within the shallow part of the curve. At maximum diastole, further expansion of the heart is resisted by the increasing slope of the compliance curve.

Figure 9:
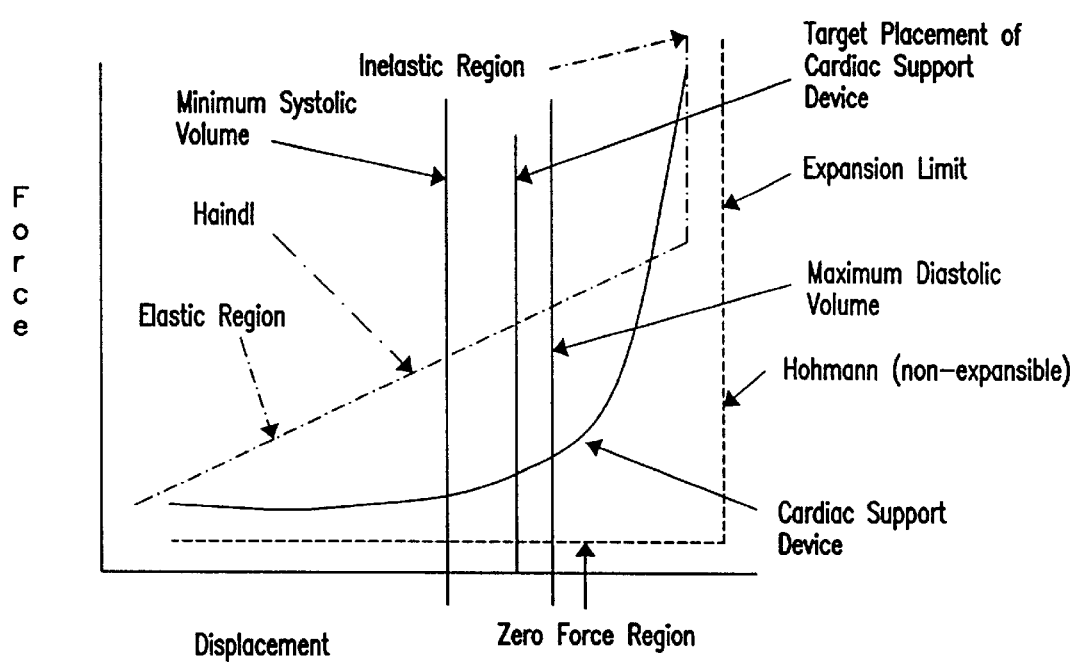
FIG. 9 shows comparative Force-Displacement plots for material suitable for use in the jacket of the invention, an elastic material and a non-elastic material.

FIG. 9 compares the compliance of the jacket of the invention with a pouch constructed from a non-compliant material, such as described in DE 295 17 393 (Hohmann), and a pouch constructed from an elastic material, such as described in PCT WO 98/58598 (Haindl).

Hohmann describes a pouch which is non-expansible. The pouch described by Hohmann does not materially present a resisting force during diastole nor does the pouch materially provide an assisting force during systole. In FIG. 9, the Hohmann material is shown in an idealized form where the pouch has no force on the heart ("zero force region") until maximum diastolic filling, where the pouch does not expand ("expansion limit").

Haindl describes a pouch that is smaller than the smallest volume of the heart and exerts a constant force on the heart which increases as the heart volume increases. As shown in FIG. 9, the material of Haindl has a progressively increasing force on the heart ("elastic region") until maximum diastolic filling, when the pouch becomes inelastic ("inelastic region") preventing further expansion.

In contrast to the pouch described by Hohmann, the material used in the jacket of the invention is compliant rather than elastic. In contrast to the pouch described by Haindl, the jacket of the invention does not apply a significant or constant force on the heart H throughout the cardiac cycle. Instead, the jacket 10 of the invention generally applies a greater pressure (e.g., about 6 mm Hg (0.8 kPa) to about 36 mm Hg (4.8 kPa) more pressure) on the heart at end diastole than at end systole.

Compliance

Figure 11:
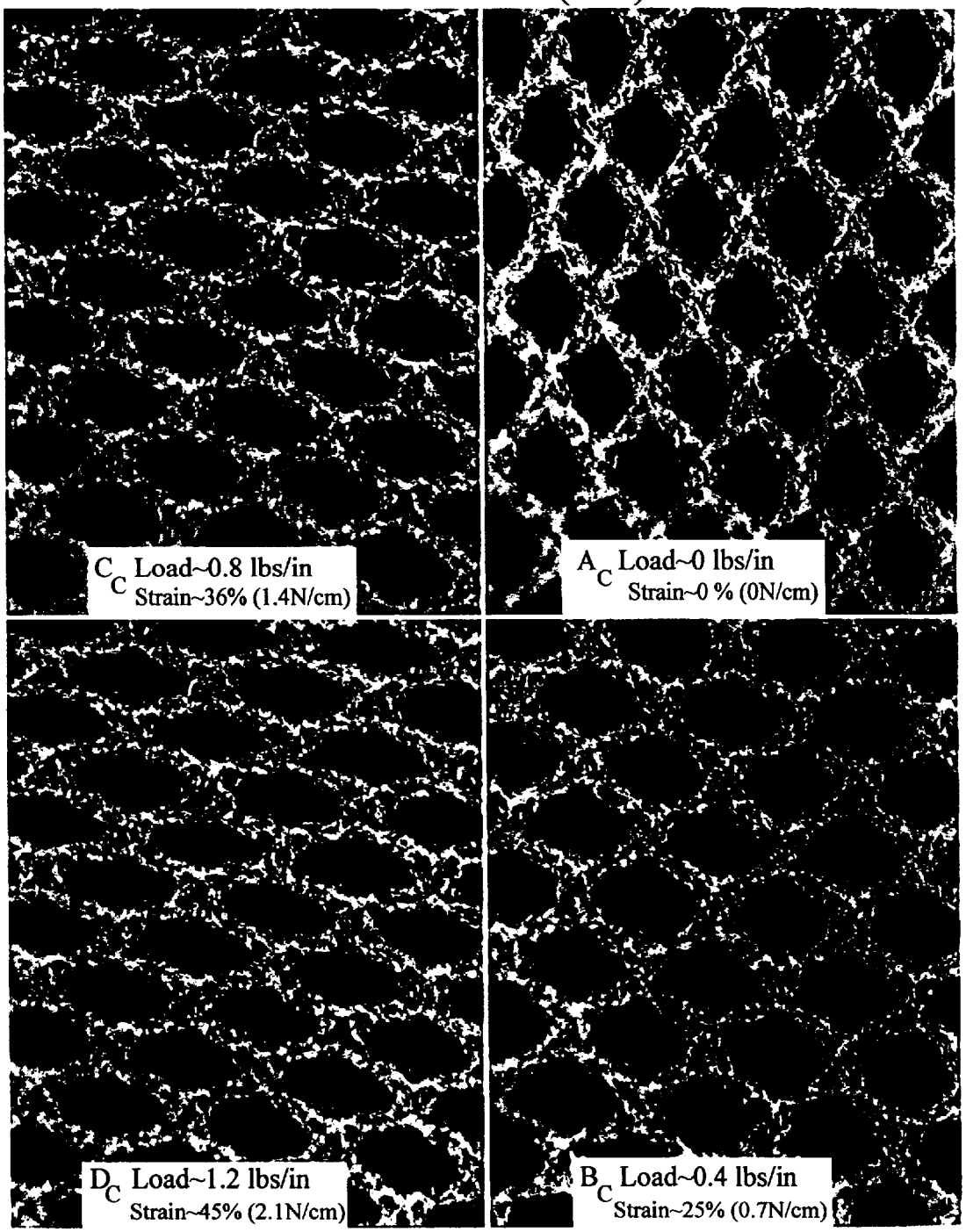
FIG. 11 is a photograph of the material from FIG. 10 loaded along the second axis of the material at points $A_C$, $B_C$, $C_C$ and $D_C$.
Figure 12:
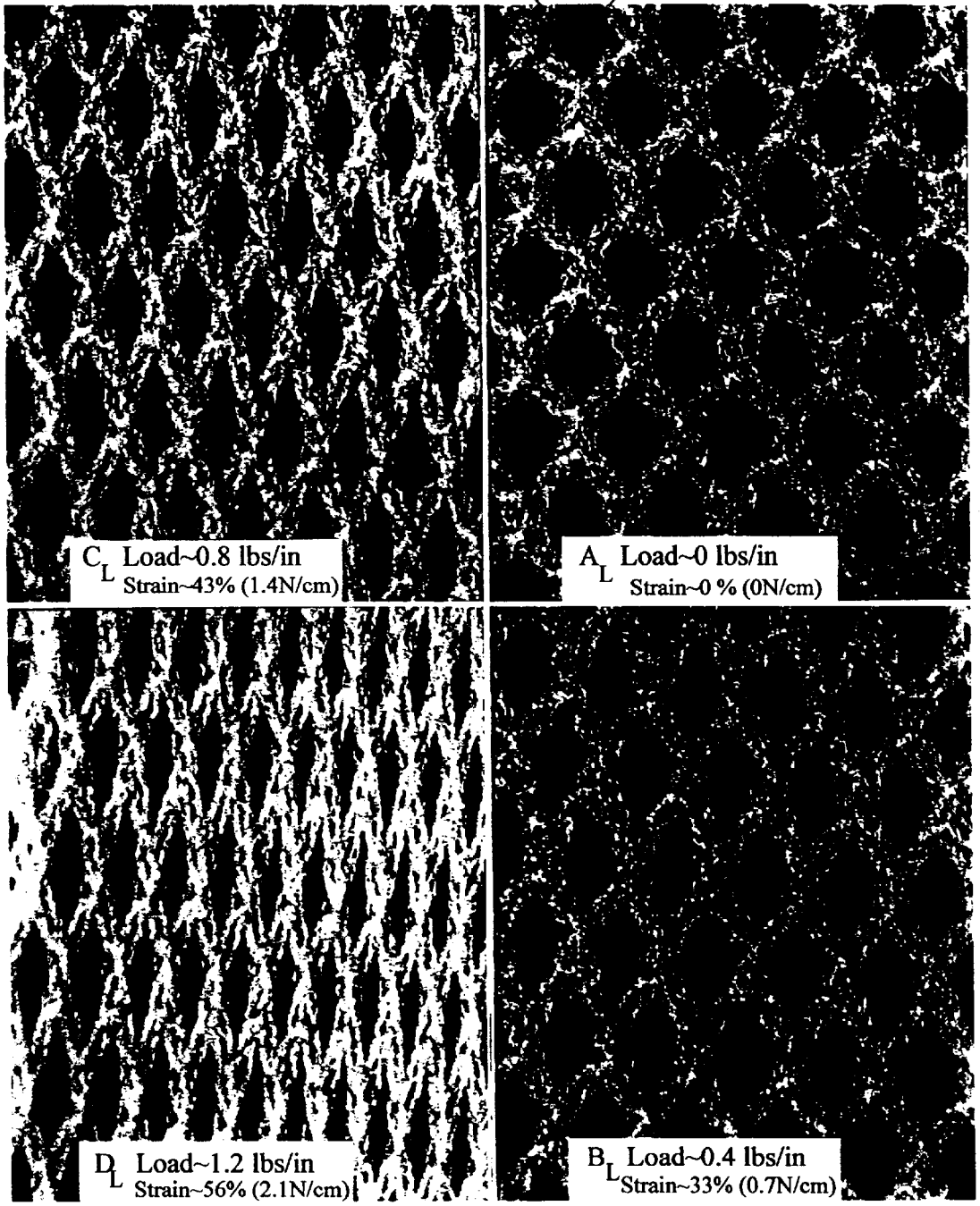
FIG. 12 is a photograph of the material from FIG. 10 loaded along the first axis of the material at points $A_L$, $B_L$, $C_L$ and $D_L$.

Generally, the jacket 10 material is formed from intertwined fibers 20 which are made up of a plurality of filaments 30 (See, e.g., FIGS. 6, 11 and 12). The compliance of the material may be due to a variety of factors, including, but not limited to, the compliance of the individual filaments 30 that make up the fibers 20, the relative movement of the filaments 30 within a fiber 20, and/or the relative movement of the intertwined fibers 20 when subjected to load.

Additionally, the compliance of the material may be affected by the shape of the heart, the manner in which the jacket 10 is fitted on the heart H and tissue fibrosis. Fibrosis tends to reduce the acute compliance of the material by preventing the openings of the fabric from geometrically changing shape.

The compliant nature of the jacket material can be easily contrasted with elastomeric material. Whereas the compliant material of the jacket preferably expands linearly up to about 30% to 50%, and elastically up to 70% without undergoing significant plastic deformation or failure, elastomeric material can be stretched repeatedly to at least twice its original length (200%), and upon release of the load, will return without force to its approximate original length. Rubber and spandex are examples of elastomeric materials. The force of the recoil depends upon the density of the elastomeric fibers within the material.

Compliance due to the relative movement (e.g., geometric deformation of the fabric openings) of the intertwined fibers 20 may be affected by the manner in which the fibers 20 are entwined. For example, a knit material will tend to be more compliant than a woven material because the loops of the knit are capable of deforming (e.g., widening or lengthening) to accommodate applied stress. In comparison, woven materials tend to have less elongation unless elastomeric fibers are used. Knit material also tends to recover well from deformation because the loops attempt to return to their original positions. The looped configuration of the fibers accommodates this recovery more readily than does the interwoven configuration found in woven materials. The ease and quickness with which elastic recovery takes place is also dependent on the fiber composition. The fibers 20 of the jacket 10 material may be entwined as a knit (for example, a warp knit) or as a weave. Preferably, the fibers 20 of the jacket 10 material are entwined as a knit.

Compliance due to the relative movement of the intertwined fibers 20 can be observed by the deformation of the structure of the fibers 20 within the material. Compliance can also be characterized using MTS Sintech test equipment. At a given load, the strain refers to the percentage increase in length of the fabric in that direction with the load applied. Preferably, the internal volume 16 of the jacket 10 is capable of multiaxial expansion up to about 30%, more typically between about 10% and 20%, in response to a load or stress up to about 5 pounds per inch (9 N/cm) without significant plastic deformation or failure.

Figure 10:
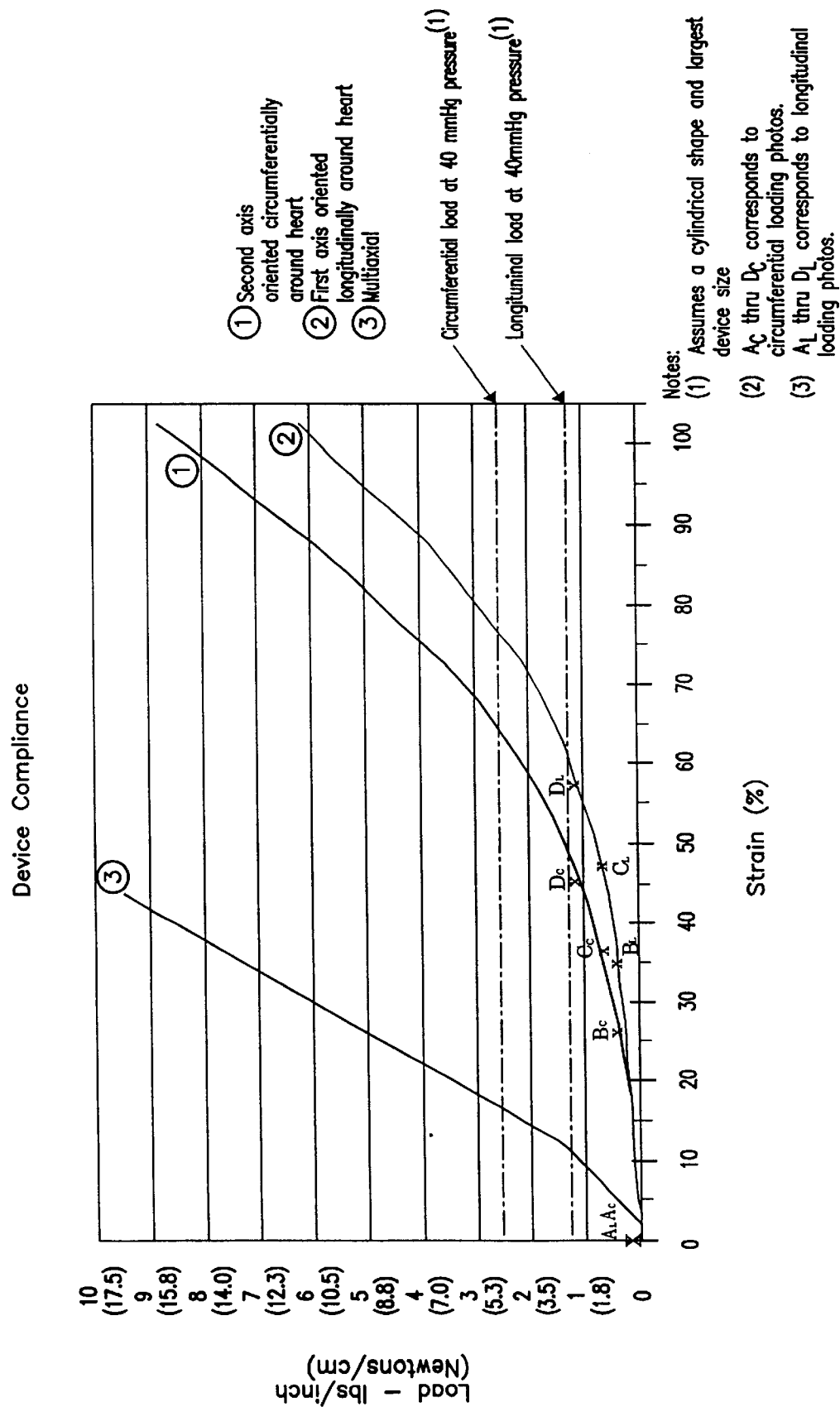
FIG. 10 is a Force-Strain plot of material suitable for use in the jacket of the invention in which the load is exerted uniaxially, along both a first axis and second axis of the fabric and multiaxially.

FIG. 10 is a plot showing the uniaxial compliance along a first axis and along a second axis perpendicular to the first axis and the multiaxial compliance of a material suitable for use in the jacket 10. The compliance parallel to the first axis of the fabric is slightly greater than the compliance perpendicular to the first axis (parallel to the second axis) of the fabric and the multiaxial compliance is significantly lower than either uniaxial compliance. Preferably, the first axis (with slightly greater compliance) is oriented longitudinally round the heart and the second axis (with slightly less compliance) is oriented circumferentially around the heart.

As shown in FIG. 10, between 20% and 40% strain, the slope of the compliance curve for the multiaxial case is 3 to 4 times greater than either uniaxial compliance curve. However, between 70% and 100% strain, the extrapolated multiaxial compliance curve slope is only 1.3 to 1.4 times greater than either uniaxial compliance curve. This indicates that the limiting stiffness of the fabric in multiaxial or uniaxial loading is similar. However, strain to reach that constraint is dependent upon loading direction.

Compliance due to the relative movement of the intertwined fibers 20 under uniaxial tension with no lateral constraint is depicted in FIGS. 11 and 12. FIG. 12 shows a knit exposed to a load in the first uniaxial direction, again with no lateral constraint (load is applied vertical with reference to the photograph). FIG. 11 shows the same knit exposed to a load in a second uniaxial direction (perpendicular to the load in FIG. 12) with no lateral constraint (load is applied horizontal with reference to the photograph). A comparison of FIGS. 11 and 12 shows that the fabric compliance along one axis (vertical with reference to the photograph) of the fabric is greater than the compliance perpendicular to that axis (horizontal with reference to the photograph). Preferably, the uniaxial compliance along a first axis (with no lateral constraint) is between about 30% and 40% when exposed to a load between about 0.1 pounds per inch (0.2 N/cm) to about 0.5 pounds per inch (0.9 N/cm); between about 40% and 50% when exposed to a load between about 0.5 pounds per inch (0.9 N/cm) to 1.0 pounds per inch (1.8 N/cm); and between about 50% and 60% when exposed to a load between about 1.0 pounds per inch (1.8 N/cm) and 1.5 pounds per inch (2.6 N/cm). Preferably, the uniaxial strain along a second axis of the fabric (perpendicular to the first axis, with no lateral constraint) is about 20% to about 30% when exposed to a load between about 0.1 pounds per inch (0.2 N/cm) to about 0.5 pounds per inch (0.9 N/cm); about 30% and 40% when exposed to a load between about 0.5 pounds per inch (0.9 N/cm) to about 1.0 pounds per inch (1.8 N/cm); and between about 40% and 50% when exposed to a load between about 1.0 pounds per inch (1.8 N/cm) and 1.5 pounds per inch (2.6 N/cm).

Four locations (A, B, C and D) are identified on both uniaxial curves in FIG. 10. These locations correspond approximately to the loads applied to the fabric in the photos of FIGS. 11 and 12. For both uniaxial directions, as the fabric load increases from $A_c$ to $D_c$ and from $A_L$ to $D_L$ the compliance curve is fairly flat. The load is predominantly accommodated by linearization of filament 30 and fiber 20 crimp and geometric distortion of the knit pattern. The photos in FIGS. 11 and 12 illustrate the distortion of the knit fabric as the openings in the fabric collapse. For example, the looping configuration of a warp knit allows the openings to collapse more along a first axis (e.g., along the warp direction) as compared to a second axis, perpendicular to the first axis (e.g., along the weft direction). This is the reason for the slightly greater compliance in the warp direction. Beyond points $D_c$ and $D_L$, the fabric becomes less compliant due to little remaining geometric distortion. The compliance curves become linear and nearly parallel to each other beyond about 80% strain. The compliance in this portion of each curve is primarily due to the elongation of the poly (ethylene terephthalate) (e.g., polyester) filaments in the fibers after the filament crimp has been removed.

As shown in FIG. 10, multiaxial loading of the fabric causes the fabric to be generally less compliant due to the inability of the fabric to geometrically deform. The multi-axial compliance of the jacket 10 material up to 12% strain is essentially linear. The slight nonlinear portion of the curve is primarily due to yarn crimp and tightening of the loops that form the geometric structure. Beyond about 12% strain, the curve is linear and is controlled by the elongation of the filaments within the fiber. Generally, the slope of the compliance curve is 30% to 40% less compliant than either of the uniaxial compliance curves.

Preferably, the knit is a so-called "Atlas knit" well known in the fabric industry. The Atlas knit is described in Paling, *Warp Knitting Technology*, p. 111, Columbine Press (Publishers) Ltd., Buxton, Great Britain (1970). The Atlas knit is a knit of fibers 20 having directional expansion properties. As shown in FIGS. 6, 11 and 12, the intertwined fibers 20 include a plurality of longitudinally extending filaments 30, wherein opposing surfaces of said multi-filament fibers 20 define a cell structure. The fibers 20 of the fabric 18 are woven into two sets of fiber strands 21a, 21b having longitudinal axes $X_a$ and $X_b$. The strands 21a, 21b are interlaced to form the fabric 18 with strands 21a generally parallel and spaced apart and with strands 21b generally parallel and spaced apart.

Figure 7:
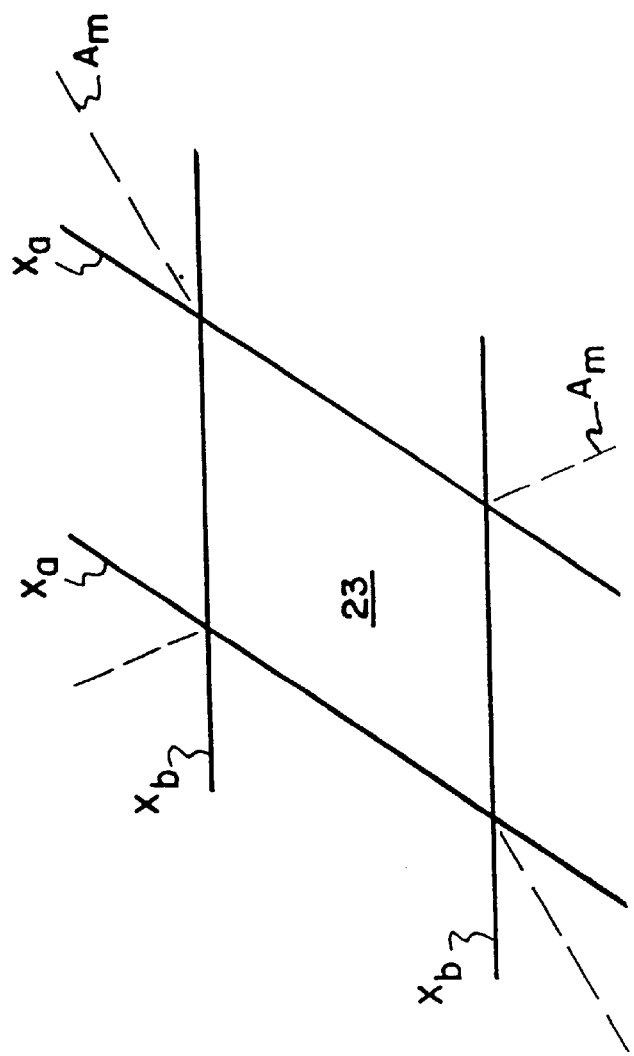
FIG. 7 is a schematic view of the material of FIG. 6.

For ease of illustration, fabric 18 is schematically shown in FIG. 7 with the axis of the strands 21a, 21b only being shown. The strands 21a, 21b are interlaced with the axes $X_a$ and $X_b$ defining a diamond-shaped open cell 23 having diagonal axes $A_m$. In a preferred embodiment, the axes $A_m$ are 5 mm in length when the fabric 18 is at rest and not stretched. The fabric 18 can stretch in response to a force. For any given force, the fabric 18 stretches most when the force is applied parallel to the diagonal axes $A_m$. The fabric 18 stretches least when the force is applied parallel to the strand axes $X_a$ and $X_b$. The jacket 10 is constructed for the material of the knit to be directionally aligned for a diagonal axis $A_m$ to be parallel to the heart's longitudinal axis AA–BB.

FIG. 6 illustrates the knit 18 in a rest state. FIGS. 11 and 12 illustrate a knit exposed to a variety of loads in a first uniaxial direction (FIG. 12), or a second uniaxial direction (FIG. 11), perpendicular to the first uniaxial direction. The directional compliance of the knit material is apparent from a comparison of FIG. 11 and FIG. 12 (e.g., a load in one direction does not produce the same strain as a load in the perpendicular direction).

Figure 13:
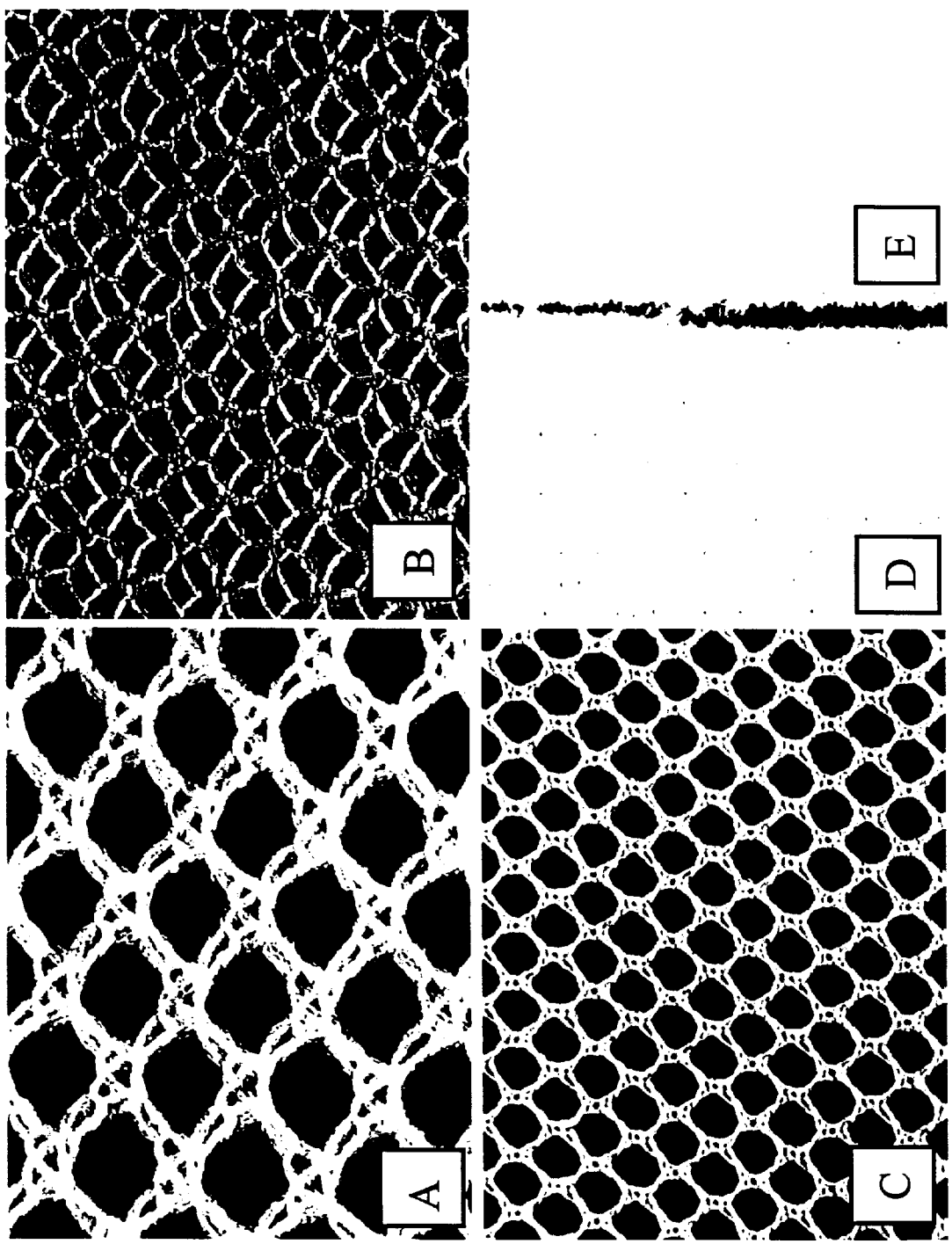
FIG. 13 is a photograph of a variety of materials.

FIG. 13 displays photographs of a variety of fabrics: (A) a knit fabric (thickness: 0.018 in.) suitable for use in the jacket of the invention; (B) a monofilament polypropylene mesh fabric (thickness: 0.026 in.), commercially available under the name Marlex (C. R. Bard, Inc., New Jersey); (C) a polyester mesh (thickness: 0.008 in.), commercially available under the name Lars Mesh (Meadox of Boston Scientific); (D) a stretch polyester fabric (thickness: 0.027 in.), commercially available as Meadox from Boston Scientific; and (E) a double velour material (thickness: 0.048 in.), commercially available under the name Cooley Double Velour (Meadox of Boston Scientific). The results of uniaxial and multiaxial compliance testing of these materials are shown in FIGS. 14 and 15, respectively.

Figure 14:
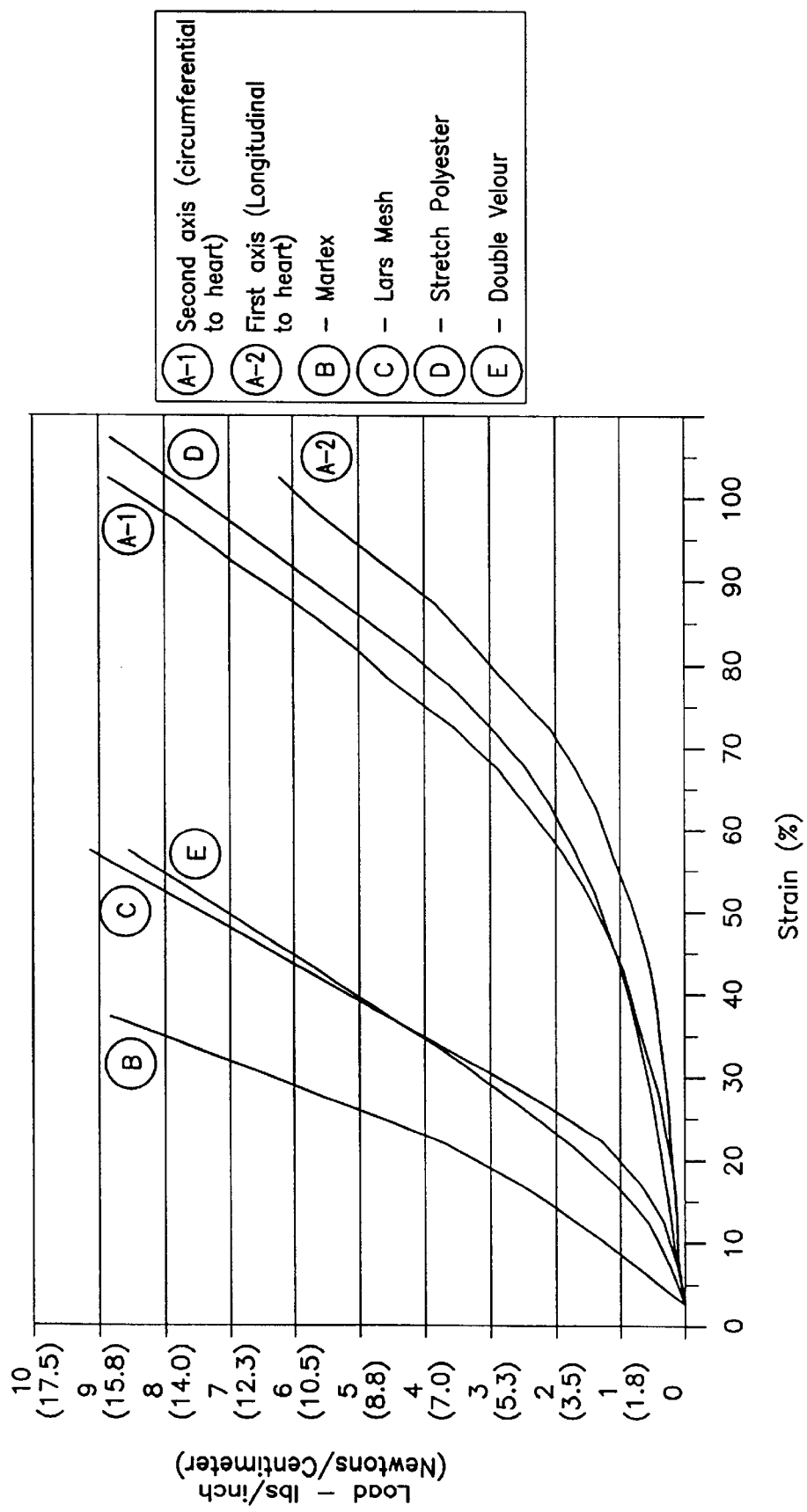
FIG. 14 is a Force-Strain plot of the uniaxial compliance for the materials shown in FIG. 13'

In FIG. 14, the Marlex, Lars and double velour are less compliant under uniaxial tension while the fabric with a uniaxial compliance most similar to the material used in the jacket 10 of the invention is the Meadox stretch polyester. It is slightly more compliant than either uniaxial strains of the material used in the jacket 10 at low stress. At high stress, the stretch polyester has a compliance slope nearly parallel and offset by about 5% to the right of the second axis uniaxial curve of the fabric used in the jacket 10 of the invention.

Figure 15:
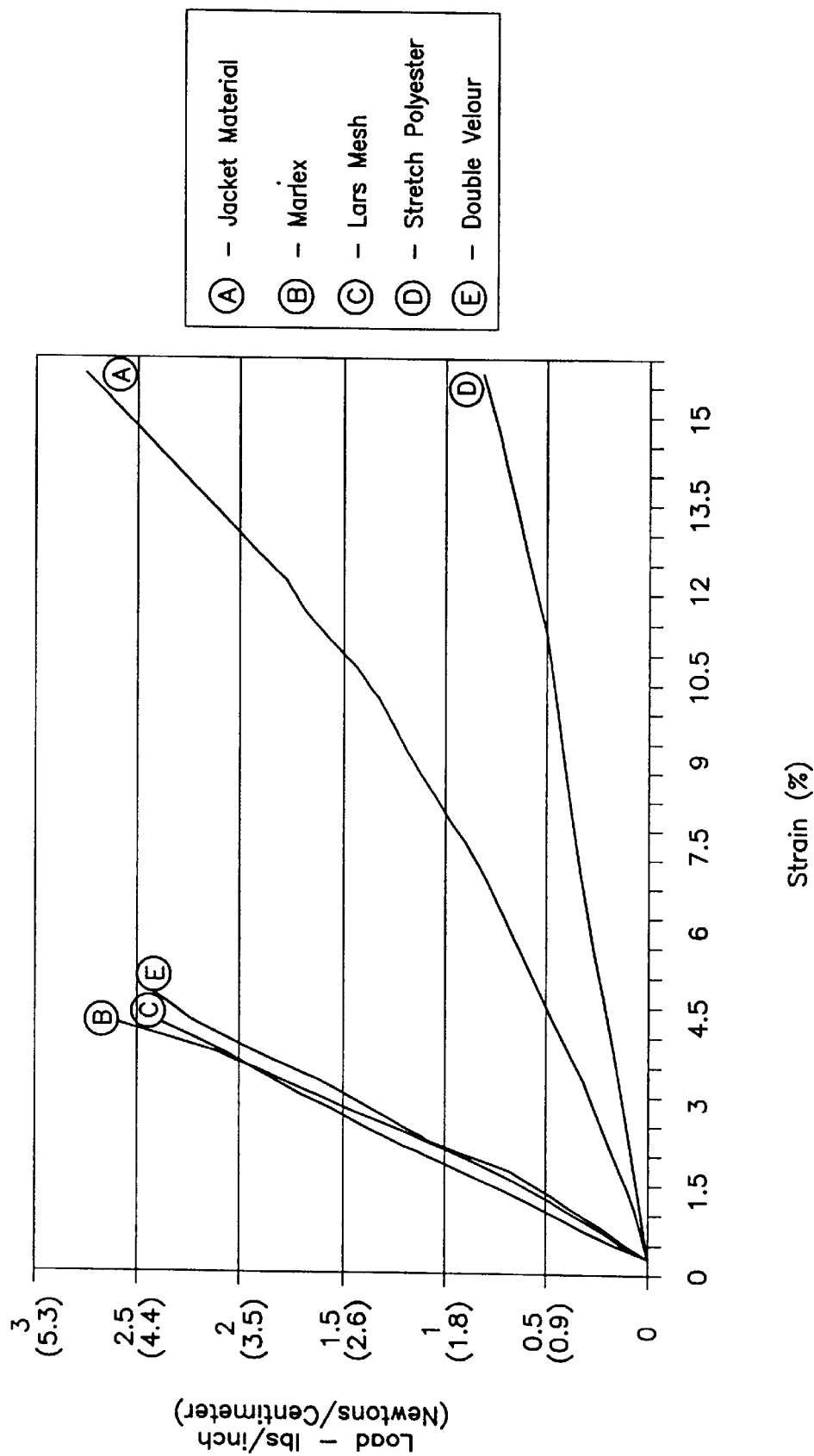
FIG. 15 is a Force-Strain plot of the multiaxial compliance for the materials shown in FIG. 13'

The five fabrics were also tested under multiaxial loading and the compliance is plotted in FIG. 15. Under multiaxial loading the Meadox stretch polyester shows the greatest compliance. The slope of the curve at about 12% strain is nearly four times greater for the fabric used in the jacket 10 of the invention than the slope for the stretch polyester. The multiaxial compliance of the other three commercial fabrics are again much stiffer and nearly indistinguishable from one another. They all have compliance curves that are more than double the stiffness of the fabric used in the jacket 10 of the invention at low strain. None of the commercial fabrics tested provide desirable levels of compliance for both uniaxial and multiaxial loading, yet provide the constraining support required at higher strains to prevent continued heart dilation for this application. Only the stretch polyester appears to have compliance that is similar to the jacket 10 fabric, allowing conformance to the heart. However, at larger strains the stretch polyester does not stiffen under multiaxial loads like the fabric used in the jacket 10, resulting in less constraining support.

The knit material has numerous advantages. Such a material is flexible to permit unrestricted movement of the heart H (other than the desired constraint on circumferential expansion). The material is open defining a plurality of interstitial spaces for fluid permeability as well as minimizing the amount of surface area of direct contact between the heart H and the material of the jacket 10 (thereby minimizing areas of irritation or abrasion) to minimize fibrosis and scar tissue.

The open areas of the knit construction also allows for electrical connection between the heart and surrounding tissue for passage of electrical current to and from the heart. For example, although the knit material is an electrical insulator, the open knit construction is sufficiently electrically permeable to permit the use of trans-chest defibrillation of the heart. Also, the open, flexible construction permits passage of electrical elements (e.g., pacer leads) through the jacket. Additionally, the open construction permits other procedures, e.g., coronary bypass, to be performed without removal of the jacket.

A large open area for cells 23 is desirable to minimize the amount of surface area of the heart H in contact with the material of the jacket 10 (thereby reducing fibrosis). However, if the cell area 23 is too large, localized aneurysm can form. Also, a strand 21a, 21b can overly a coronary vessel with sufficient force to partially block the vessel. A smaller cell size increases the number of strands thereby decreasing the restricting force per strand. In a preferred embodiment, the cell area CA of cells in a particular row directly correlates with a cross-sectional circumferential dimension of the heart that the row of cells surrounds relative to other cross-sectional circumferential dimensions. That is, the greater the cross-sectional circumferential dimension, the greater the area of the cells in the row of cells directly overlying that cross-sectional circumferential dimension. By "correlating" cell area with cross-sectional circumferential dimension of the heart, the cell area is determined as a function of the cross-sectional circumferential dimension of the heart. The cell area is determined so that when the weave material is applied to the heart or is shaped into a jacket and applied to the heart, each cell can widen sufficiently to provide desirable cardiac constraint. Thus, the cell area will be smaller for cells in a row applied over a region of the heart that has a smaller cross-sectional circumferential dimension than the cell area of cells in a row applied over a region of the heart having a larger cross-sectional circumferential dimension. The appropriate maximum cell area may be, for example, 1 to 100 mm$^2$, typically 16 to 85 mm$^2$. The maximum cell area is the area of a cell 23 after the material of the jacket 10 is fully stretched and adjusted to the maximum adjusted volume on the heart H as previously described.

Young's Modulus

Prior to discussing the contribution of filament elasticity and fiber structure to the compliance of the jacket material, an overview of Young's Modulus will be provided.

Figure 16:
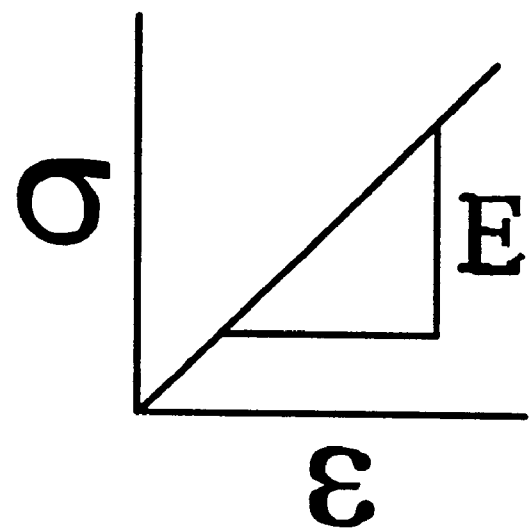
FIG. 16 is an illustrative Stress-Strain plot showing a linear elastic slope according to Hooke's Law.

Stress refers to the force (F) normalized by the cross sectional area (A) of an object. Stress can be represented by the following formula: F/A. For fabrics, unit load is commonly used in lieu of stress. The unit load is force (F) normalized by the width of a unit measure of fabric. Strain is defined as the change in length of the object normalized by the initial length. Strain can be represented by the following formula: $(l_1-l_0)/l_0$. Thus, if stress (or unit load) is plotted versus strain, the slope of the line in the elastic/linear range of the material gives the elastic modulus or Young's modulus (E) of the object. (FIG. 16).

The stress-strain curve begins at zero stress and stops at the amount of force which ruptures the fiber. The shape, length and height of a stress-strain curve indicates how well a fiber resists elongation, how far it will elongate before rupturing and how strong it is. The curve also establishes the point at which a fiber will not recover fully from an applied stress.

According to Hooke's law, (at relatively low stress) the strain is proportional to stress and therefore the ratio of the two is a constant that may be used to indicate the elasticity of the object. Young's Modulus may be loosely defined as the force required to elongate an object. The elastic modulus can be calculated from measurements obtained by pulling a sample of the object in a tensile testing machine. Young's Modulus for some polymers is provided in Table 1, below.

TABLE 1

| Young's Modulus for Some Polymers | | |
|---|---|---|
| Material | Modulus (Kpsi) | Modulus (GPa) |
| Polyimides | 400–700 | 3–5 |
| Polyesters | 150–700 | 1–5 |
| Nylon | 300–600 | 2–4 |
| Polystryene | 400–500 | 3–3.4 |
| Polyethylene | 30–100 | 0.2–0.7 |

The linear portion of the curve generally indicates the elastic behavior of the material. Strains induced in the material due to a stress within the linear portion are totally recoverable once the stress is removed. The strain is thus referred to as elastic. When the initial linear segment of the stress-strain curve rises steeply, a relatively large increase in stress produces a relatively small increase in strain (e.g., the fiber has a high initial modulus). If the lines slopes at 45°, then there is a unit increase in strain for each unit increase in stress and the initial modulus of the fiber is average. As the slope decreases or the line become more horizontal, the initial modulus of the fiber becomes lower. Fibers with low initial modulus are relatively easy to elongate. A slight force results in considerable fiber lengthening. In contrast, a large force must be applied to fibers with high initial modulus for small amounts of extension to occur.

In this initial segment of the stress-strain curve, the lengthening of the fiber is (1) the result of the degree to which polymers lying at angles to the fiber axis can be moved into alignment with the axis and (2) polymers with a nonlinear configuration can be straightened. Polymers that are spiraled and folded tend to act like springs; once stress is released they attempt to return to their original configuration. Thus, low modulus fibers tend to be less oriented than high modulus fibers. Polymer slippage does not occur within the fiber during the initial modulus segment of the stress strain curve.

Figure 17:
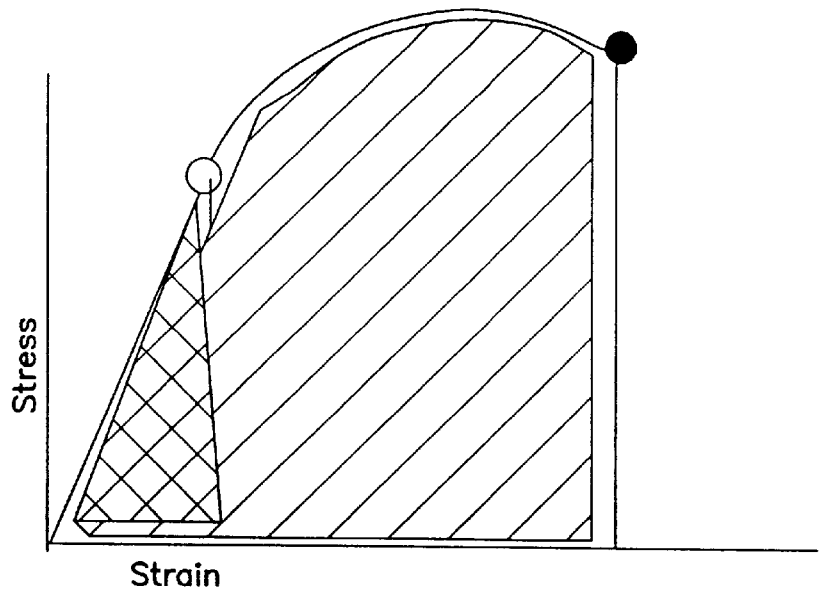
FIG. 17 is an illustrative Stress-Strain plot showing the area of resilience and the elastic limit of a material.

As the stress on an object is increased, the plot of stress versus strain becomes non-linear (FIG. 17). The elastic limit generally refers to the point where the curve begins to deviate from linearity. Beyond the elastic limit, the material undergoes plastic deformation. Unlike elastic deformation, plastic deformation is not recoverable, i.e., the change is permanent. When a load is applied to an object and the object deforms and does not return to its original length when the load is removed, the object is said to have undergone a plastic deformation. At the elastic limit, the polymers of the object begin to slip by one another as the stress becomes larger than the force of attraction between the polymers. However, when polymers are covalently cross-linked, the crosslinks work to pull the polymers back their original positions.

Fibers

Figure 18:
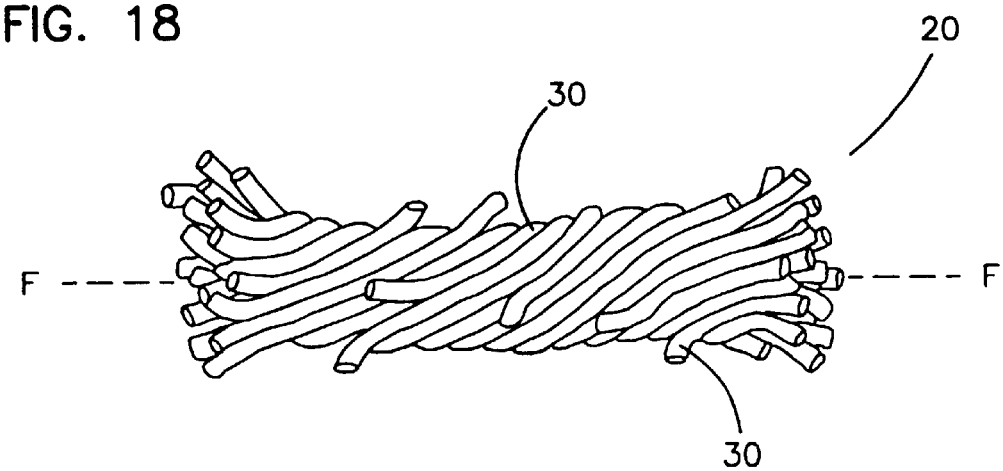
FIG. 18 is an illustration of a fiber in which the overlapping filaments are substantially aligned with the fiber axis F—F.
Figure 19:
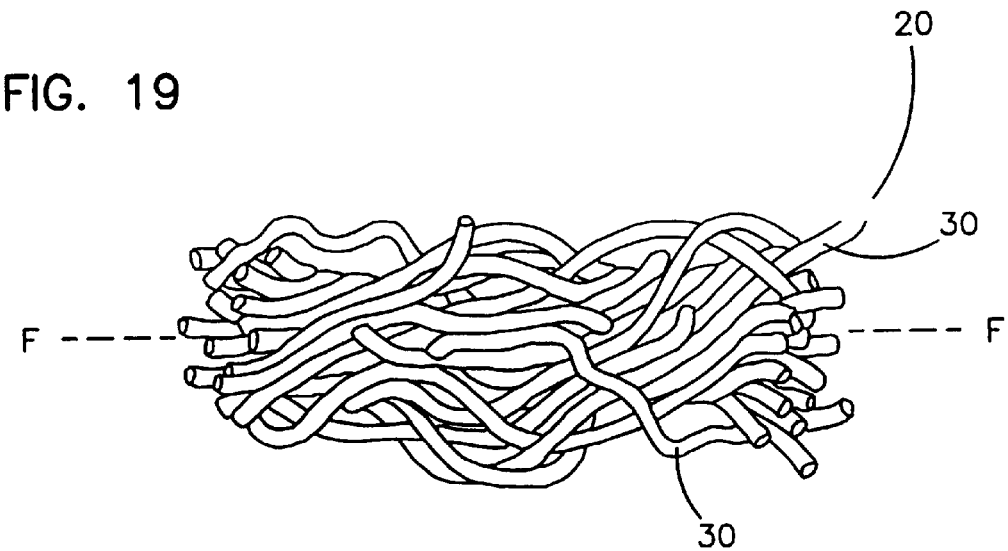
FIG. 19 is an illustration of a fiber in which the overlapping filaments are not substantially aligned with the fiber axis F—F.
Figure 20:
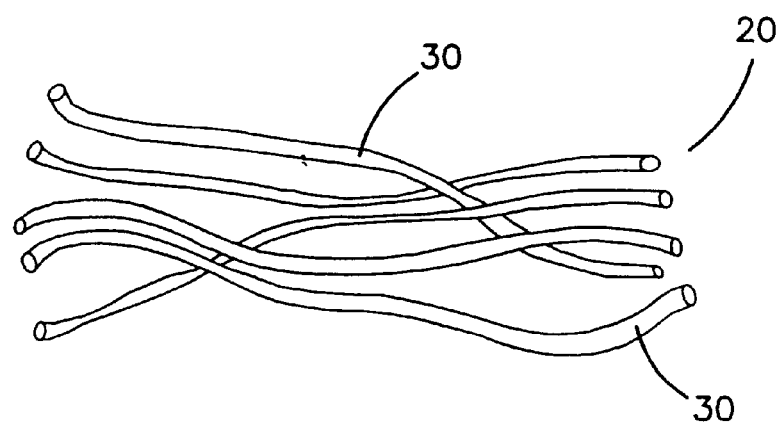
FIG. 20 is an illustration of a fiber which is composed of continuous filaments.

The compliance of the jacket 10 may also be affected by the relative movement of the filaments 30 within the fibers 20. The relative movement of the filaments 30, in turn, may be affected by the structure of the fiber 20. A fiber 20 may be composed of overlapping filaments 30 that are twisted about one another and held together by a binding mechanism (FIGS. 18 and 19) or the fiber 20 may be composed of continuous filaments 30 (or a single filament) that extend longitudinally along the length of the fiber 20 (FIG. 20), assembled with or without a twist. The fiber 20 may be composed of filaments 30 that are substantially aligned with the fiber axis F—F (FIG. 18) or the filaments 30 may lie more obliquely with respect to the fiber 20 axis (FIG. 19).

Preferably, the fiber 20 is composed of continuous filaments 30. Because continuous filaments 30 have less protruding ends, continuous filaments 30 are less likely to abrade the surface of the heart H during systole and diastole. In a fiber made of continuous filaments 30, the lengthening of the fiber 20 is generally the result of the degree to which filaments 30 lying at angles to the fiber axis F—F can be moved into alignment with the axis F—F and filaments 30 with a nonlinear configuration can be straightened. Filaments 30 that are spiraled and folded tend to act like springs; once stress is released they attempt to return to their original configuration. Overlapping filaments 30 in a fiber 20 may slip when exposed to stress, thus permanently altering or "stretching" the fiber 20.

Fibers 20 with multifilaments that are not substantially aligned are preferred, such that fabric compliance from the fiber straightening can help to accommodate expansion of the ventricles during diastole. Generally, preferred fibers include 70 Denier textured polyester.

Filaments

The elasticity of the filaments 30 which make up the fibers 20 may also affect the compliance of the jacket 10. The filaments 30 are preferably formed of a non-elastomeric material (i.e., the filament 30 does not return to its approximate original length with force), preferably the filament is constructed from a material with a moderate modulus of elasticity, more preferably between 1.0 GPa (150 Kpsi) and 5 GPa (700 Kpsi). In a preferred embodiment, the filaments 30 include 34 strands to construct the 70 Denier poly (ethylene terephthalate) (e.g., polyester) fibers 20. While poly(ethylene terephthalate) is presently preferred, other suitable materials may include polytetrafluoroethylene (PTFE), expanded PTFE (ePTFE), polypropylene, titanium and stainless steel.

With the foregoing, a device and method have been taught to treat cardiac disease. The jacket 10 constrains further undesirable circumferential enlargement of the heart while not impeding other motion of the heart H. With the benefits of the present teachings, numerous modifications are possible. For example, the jacket 10 need not be directly applied to the epicardium (i.e., outer surface of the myocardium) but could be placed over the parietal pericardium. Further, an anti-fibrosis lining (such as a PTFE coating on the fibers of the knit) could be placed between the heart H and the jacket 10. Alternatively, the fibers 20 can be coated with PTFE.

The jacket 10 is low-cost, easy to place and secure, and is convenient for use in minimally invasive procedures. The thin, flexible fabric 18 permits the jacket 10 to be collapsed and passed through a small diameter tube in a minimally invasive procedure.

The jacket 10, including the knit construction, freely permits longitudinal and circumferential contraction of the heart H (necessary for heart function). Unlike a solid wrap (such as a muscle wrap in a cardiomyoplasty procedure), the fabric 18 does not impede cardiac contraction. After fitting, the jacket 10 is inelastic to prevent further heart enlargement while permitting unrestricted inward movement of the ventricular walls. Because the jacket 10 is not constructed from an elastomeric material, it does not substantially assist the heart during systolic contraction.

The open cell structure permits access to coronary vessels for bypass procedures subsequent to placement of the jacket 10. Also, in cardiomyoplasty, the latissimus dorsi muscle has a variable and large thickness (ranging from about 1 mm to 1 cm). The material of the jacket 10 is uniformly thin (less than 1 mm thick). The thin wall construction is less susceptible to fibrosis and minimizes interference with cardiac contractile function.

Animal test studies on the device show the efficacy of the invention. Test animals were provided with the device 10 of FIG. 3. The animals' hearts were rapidly paced to induce enlargement. After six weeks, animals without the device experienced significant heart enlargement while those with the device experienced no significant enlargement. Further, animals with the device had significantly reduced mitral valve regurgitation.

In addition to the foregoing, the present invention can be used to reduce heart size at the time of placement in addition to preventing further enlargement. For example, the device can be placed on the heart and sized snugly to urge the heart to a reduced size. More preferably, the heart size can be reduced at the time of jacket placement through drugs (e.g., dobutamine, dopamine or epinephrine or any other positive inotropic agents) to reduce the heart size. The jacket of the present invention is then snugly placed on the reduced sized heart and prevents enlargement beyond the reduced size.

From the foregoing, a low cost, reduced risk method and device are taught to treat cardiac disease. The invention is adapted for use with both early and later stage congestive heart disease patients. The invention reduces the enlargement rate of the heart as well as reducing cardiac valve regurgitation.

EXAMPLES OF IMPLANT SCENARIOS

Example 1

In this example, the heart is assumed to be spherical in shape and 46 cm (18 in.) in diameter at end diastole. The device is installed around the heart and adjusted to create a uniform loading of the fabric. Because the heart is spherical in shape, the pressure is uniformly applied to the heart and resisted by the device like a spherical pressure vessel, where the load per unit width is pd/4 (Note: p=pressure, d=diameter). Since the load is uniform the multiaxial compliance curve of the fabric would be most applicable. FIG. 21 illustrates the installed condition for an end diastolic device pressure of 20 mm Hg (2.7 kPa). This corresponds to 0.6 lbs/in. fabric load for this size heart.

During systole the heart muscle contracts and the external dimension is reduced. On average, the heart reduces circumferentially by approximately 6% and longitudinally by 4% from end diastole to end systole. Thus, for the case of a 4% to 5% change in circumference and diameter is assumed. This linear dimensional change relates to a 12% to 15% external ventricular volume change for a spherical heart. At end systole, FIG. 21 shows that the circumference reduces to 44 cm (17.3 in.) and the applied pressure drops from 20 mm Hg (2.7 kPa) to 4 mm Hg (0.53 kPa). For this condition the fabric load is only 0.1 lbs/in and the device is nearly unloaded.

The pressure applied by the device is helping to offload heart wall stress throughout the cardiac cycle. This support is greatest at end diastole when the heart volume is greatest (relaxing between systolic contractions). Although the diastolic phase is considered relaxing, the myocardium may never actually completely relax. Some slight loading during diastole may not significantly restrict filling but rather serve to off load the wall stress throughout the cardiac cycle.

If the heart becomes improved and reduces in size, the device will become unloaded at end systole. Only a 16% volume reduction will result in the device being completely unloaded. If the heart continues to dilate due to continued disease progression, load support from the jacket increases dramatically. With less than 4% increase dilation, the applied pressure would double to a load of 40 mm Hg (5.3 kPa). The biaxial compliance curve of the fabric results in very significant pressure changes for relatively small volume changes.

Example 2

In this example, the heart is assumed to be cylindrical in shape and again 46 cm (18 in.) in circumference at end diastole. The device is installed around the heart and adjusted to create a primarily circumferential loading of the fabric with the end effects and longitudinal loading assumed to be negligible. Because the heart is cylindrical in shape, the circumferential load per unit width is pd/2. Note that based on the pressure vessel theory, this is twice the load resisted in the spherical shape of Example 1 for the same pressure. Since the load is only circumferential, the uniaxial compliance curve of the fabric would be most applicable. FIG. 22 illustrates the installed condition for an end diastolic device pressure of 10 mm Hg (1.3 kPa). This corresponds to 0.6 pounds per inch (1.1 N/cm) fabric load for this size heart.

Similar to Example 1, during systole the heart muscle contracts and the external dimensions of the heart are reduced. If a 6% change in circumference and diameter is assumed, along with a 4% longitudinal length change, the external ventricular volume change would be approximately 17%. At end systole, FIG. 22 shows that the circumference reduces to 44 cm (17.3 in.) and the applied pressure only drops from 10 mm Hg (1.3 kPa) to 8 mm Hg (1.1 kPa). For this condition, the fabric load is nearly unchanged from 0.6 to 0.5 pounds per inch (1.1 N/cm to 0.88 N/cm). This small load change is due to a flat compliance curve.

Similar to Example 1, the pressure applied by the device is helping to offload heart wall stress throughout the cardiac cycle. However, in this case the support from the jacket is nearly constant throughout the cardiac cycle.

For the case shown in FIG. 22, if the heart becomes improved and reduces in size, the device will continue to be supported for a volume reduction of up to 70%. This compliance/load scenario would result in longer term support than in Example 1. As the heart diameter reduces and progresses to the left on the compliance curve, the loading is gradually lowered. This will continue until a very significant 70% external volume reduction occurs. If the heart continues to dilate due to continued disease progression or exercise overload, the load support from the jacket increases dramatically with a significant increase in dilation. A 30 mm Hg (4 kPa) increase in pressure to the 40 mm Hg (5.3 kPa) design load will allow a 30% increase diametrical dilation. The uniaxial compliance curve of the fabric allows very large changes in size with relative small load changes, assuming the load remains unidirectional.

The therapy provided by the device may be a combination of Examples 1 and 2. When installed the jacked behaves as in Example 1 if it is adjusted to provide a nearly uniform load. Then as the heart improves and reduces in size, the loading may become more unidirectional if either the longitudinal or circumferential directions do not change at the same rate. This would change the compliance curve to behave more like Example 2. The actual fabric compliance curve may transition from multiaxial to uniaxial as the heart shape changes.

What is claimed is:

1. A device for treating cardiac disease of a heart having a longitudinal axis from an apex to a base and having an upper portion and a lower portion divided by an A-V groove, said heart including a valvular annulus adjacent said A-V groove and ventricular lower extremities adjacent said apex, the device comprising:

a jacket of flexible material defining a volume between an open upper end and a lower end, wherein an expansion of said flexible material is less than about 30% when said material is exposed to a load up to about 5 pounds per inch (9 N/cm);

said jacket dimensioned for said apex of said heart to be inserted into said volume through said open upper end and for said jacket to be slipped over said heart, said jacket further dimensioned for said jacket to have a longitudinal dimension between said upper and lower ends sufficient for said jacket to constrain said lower portion with said jacket constraining said valvular annulus;

said jacket adapted to be secured to said heart with said jacket having portions disposed on opposite sides of the heart between said valvular annulus and said ventricular lower extremities; and said jacket adapted to be expandibly adjusted on said heart to snugly conform to an external geometry of said heart to constrain circumferential expansion of said heart and permit substantially unimpeded contraction of said heart during systole.

2. A device according to claim 1 wherein:

an expansion of said material along a first axis of said material is between about 30% and 40% when exposed to a uniaxial load between about 0.1 pounds per inch (0.2 N/cm) to about 0.5 pounds per inch (0.9 N/cm) with no lateral constraint;

an expansion of said material along a second axis of said material is between about 20% and 30% when exposed to a uniaxial load between about 0.1 pounds per inch (0.2 N/cm) to about 0.5 pounds per inch (0.9 N/cm) with no lateral constraint; and said material oriented for said second axis to extend circumferentially around said heart and wherein said first axis is perpendicular to second axis.

3. A device according to claim 1 wherein said jacket is open at said lower end.

4. A device according to claim 1 wherein said jacket is closed at said lower end.

5. A device according to claim 1 wherein said material comprises intertwined fibers.

6. A device according to claim 5 wherein said material is a knit material.

7. A device according to claim 6 wherein said material is a warp knit.

8. A device according to claim 6 wherein said material is an Atlas knit.

9. A device according to claim 5 wherein said material is a weave.

10. A device according to claim 5 wherein said intertwined fibers comprise a plurality of longitudinally extending filaments.

11. A device according to claim 1 wherein said material is selected from a the group consisting of polytetrafluoroethylene, expanded polytetrafluoroethylene, polypropylene, poly(ethylene terephthalate), titanium and stainless steel.

12. A device according to claim 1 wherein said material is formed of elongated fibers selected from a the group consisting of polytetrafluoroethylene, expanded polytetrafluoroethylene, polypropylene, poly(ethylene terephthalate), titanium and stainless steel.

13. A method for treating cardiac disease of a heart having a longitudinal axis from an apex to a base and having an upper portion and a lower portion divided by an A-V groove, the heart including a valvular annulus adjacent the A-V groove and ventricular lower extremities adjacent the apex; the method comprising:

(a) providing a jacket of flexible material defining a volume between an open upper end and a lower end, wherein an expansion of the flexible material is less than about 30% when the material is exposed to a load up to about 5 pounds per inch (9 N/cm);

(b) slipping the jacket over the head:

(c) constraining the valvular annulus with the jacket;

(d) securing the jacket to the heart with portions of the jacket disposed on opposite sides of the heart between the valvular annulus and the ventricular lower extremities; and (e) expandibly adjusting the jacket on the heart to conform the jacket to an external geometry of the heart to constrain circumferential expansion of the heart and permit substantially unimpeded contraction of the head during systole.

14. A method according to claim 13 herein:

(a) said step of providing a jacket includes providing a jacket having a multiaxial expansion of the flexible material being less than about 30% when the material is exposed to a load up to about 5 pounds per inch (9 N/cm).

15. A method according to claim 13 wherein:

(a) said step of securing the jacket includes covering a lower end of the heart.

16. A method according to claim 13 wherein:

(a) said step of securing the jacket includes leaving a lower end of the heart exposed.

17. A method according to claim 13 wherein:

(a) said step of providing a jacket includes providing a jacket having:

(i) an expansion of material along a first axis between about 30% and 40% when exposed to a uniaxial load between about 0.1 pounds per inch (0.2 N/cm) to about 0.5 pounds per inch (0.9 N/cm) with no lateral constraint;

(ii) an expansion of material along a second axis between about 20% and 30% when exposed to a uniaxial load between about 0.1 pounds per inch (0.2 N/cm) to about 0.5 pounds per inch (0.9 N/cm) with no lateral constraint.

18. A method according to claim 17 wherein:

(a) said step of securing the jacket includes orienting the material for such that the second axis extends circumferentially around the heart; the first axis being perpendicular to the second axis.

* * * * *

UNITED STATES PATENT AND TRADEMARK OFFICE
CERTIFICATE OF CORRECTION

PATENT NO. : 6,682,476 B2
DATED : January 27, 2004
INVENTOR(S) : Alferness et al.

It is certified that error appears in the above-identified patent and that said Letters Patent is hereby corrected as shown below:

Column 6,
Line 25, "healthy, heart" should read -- healthy heart --

Column 8,
Line 11, "noted-that" should read -- noted that --
Line 38, "attachment (to the parietal" should read -- attachment to the parietal --

Column 20,
Lines 62 and 67, "from a the group" should read -- from the group --

Column 21,
Line 15, "over the head:" should read -- over the heart: --
Line 24, "of the head" should read -- of the heart --
Line 26, "herein:" should read -- wherein --

Signed and Sealed this

Eighteenth Day of May, 2004

JON W. DUDAS
*Acting Director of the United States Patent and Trademark Office*